US006908990B2

(12) United States Patent  
Edlund

(10) Patent No.: US 6,908,990 B2  
(45) Date of Patent: Jun. 21, 2005

(54) INSULIN PROMOTER FACTOR, AND USES RELATED THERETO

(75) Inventor: Thomas Edlund, Umeå (SE)

(73) Assignee: ES Cell International Pte Ltd., Singapore (SG)

( * ) Notice: Subject to any disclaimer, the term of this patent is extended or adjusted under 35 U.S.C. 154(b) by 4 days.

(21) Appl. No.: 09/759,847

(22) Filed: Jan. 12, 2001

(65) Prior Publication Data

US 2002/0082410 A1 Jun. 27, 2002

Related U.S. Application Data

(63) Continuation of application No. 09/031,898, filed on Feb. 27, 1998, now Pat. No. 6,197,945, which is a continuation of application No. 08/320,148, filed on Oct. 7, 1994, now Pat. No. 5,849,989.

(51) Int. Cl.$^7$ .................... C07H 21/04; C07K 17/00; C12Q 1/68; G01N 33/53; C12P 19/34
(52) U.S. Cl. ................ 536/23.1; 530/350; 435/6; 435/7.1; 435/91.7; 536/24.3; 536/24.33
(58) Field of Search ................. 536/23.1, 24.3, 536/24.33, 24.32; 435/6, 91.1, 91.2, 7.1, 7.8, 7.92; 530/350

(56) References Cited

U.S. PATENT DOCUMENTS 5,858,973 A * 1/1999 Habener et al. ............ 514/12
6,197,945 B1 * 3/2001 Edlund ...................... 536/23.1

OTHER PUBLICATIONS

Barton, "Protein sequence alignment and database scanning", Protein Structure Prediction: A Practical Approach, IRL Press, New York: 31–63 (1996).
Brinster, R.L. et al., "Factors affecting the efficiency of introducing foreign DNA into mice microinjecting eggs", PNAS U 82: 4438–4442 (1985).
George et al., Current Methods in Sequence Comparison and Analysis, Marcromolecular Sequencing and Synthesis: Selected Methods and Applications, Alan R. Liss, Inc., New York: 127–149 (1988).
Hammer, R. E. et al., "Production of transgenic rabbits, sheep, and pigs by microinjection", Nature 315: 680–683 (1985).

Ishaguro, S. et al., "Characterization of a cDNA encoding a novel DNA–binding protein, SPF1, that recognizes SP8 sequences in the 5' upstream regions of genes coding for sporamin and β–amylase from sweet potato", Mol. Gen. Genet. 244: 563–571 (1994).
Jaenisch, R., "Transgenic Animals", Science 240: 1468–1474 (1988).
Langer, R. et al., "Tissue Engineering", Science 260: 920–926 (1993).
McGinnis, W. et al., "Homeobox Genes and Axial Patterning", Cell 68: 283–302 (1992).
Ohlsson, H. et al., "Novel Insulin Promoter–and Enhancer–Binding Proteins That Discriminate Btween Pancreatic α–and β–Cells", Mol. Endocrinol. 5 (7): 897–904 (1991).
Ohlsson et al., "IPF1, a homeodomain–containing transactivator of the insulin gene", EMBO J. 12 (11): 4251–4259 (1993).
Sakoyama, Y. et al., "Cloning of Rat Homeobox Genes", Biochem. Genet. 32 (9/10): 351–360 (1994).
Serrano M. et al., "A new regulatory motif in cell–cycle control causing specific inhibition of cyclin D/CDK4", Nature 366: 704–707 (1993).
Tomlinson, C. et al., "Ectoderm nuclei from sea urchin embroys contain a Spec–DNA binding protein similar to the vertebrate transcription factor USF", Development 110: 259–272 (1990).
Walker, M.D. et al., "Cell–Specific Expression Controlled by the 5' Flanking Region of Insulin and Chymotrypsin Genes", Nature 306: 557–561 (1983).
Wall, R.J. et al., "Development of Porcine Ova That Were Centrifuged to Permit Visualization of Pronuclei and Nuclei", Biol. of Reprod. 32: 645–651 (1985).
Watson, J.D. et al., Molecular Biology of the Gene, $4^{th}$ ed., 1: 313 (1987).
Webster's Ninth New Collegiate Dictionary: 366 (1990).

* cited by examiner

Primary Examiner—Kenneth R. Horlick
Assistant Examiner—Cynthia Wilder
(74) Attorney, Agent, or Firm—Ropes & Gray LLP

(57) ABSTRACT

The present invention relates to the discovery in eukaryotic cells, particularly mammalian cells, of novel a transcriptional regulatory factor, referred to hereinafter as "Insulin Promoter Factor 1" or "Ipf1".

11 Claims, 4 Drawing Sheets

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
         (A) LENGTH: 1313 base pairs
         (B) TYPE: nucleic acid
         (C) STRANDEDNESS: both
         (D) TOPOLOGY: linear (ii) MOLECULE TYPE: cDNA (ix) FEATURE:
         (A) NAME/KEY: CDS
         (B) LOCATION: 128..979

(xi) SEQUENCE DESCRIPTION: SEQ ID NO: 1:

```
CAGGAGAGCA GTGGAGAACT GTCAAAGCGA TCTGGGGTGG CGTAGAGAGT CCGCGAGCCA         60

CCCAGCGCCT AAGGCCTGGC TTGTAGCTCC GACCCGGGGC TGCTGGCCCC AAGTGCCGGC        120

TGCCACC ATG AAC AGT GAG GAG CAG TAC TAC GCG GCC ACA CAG CTC TAC         169
        Met Asn Ser Glu Glu Gln Tyr Tyr Ala Ala Thr Gln Leu Tyr
          1               5                  10

AAG GAC CCG TGC GCA TTC CAG AGG GGC CCG GTG CCA GAG TTC AGC GCT         217
Lys Asp Pro Cys Ala Phe Gln Arg Gly Pro Val Pro Glu Phe Ser Ala
 15              20                  25                  30

AAC CCC CCT GCG TGC CTG TAC ATG GGC CGC CAG CCC CCA CCT CCG CCG         265
Asn Pro Pro Ala Cys Leu Tyr Met Gly Arg Gln Pro Pro Pro Pro Pro
                 35                  40                  45

CCA CCC CAG TTT ACA AGC TCG CTG GGA TCA CTG GAG CAG GGA AGT CCT         313
Pro Pro Gln Phe Thr Ser Ser Leu Gly Ser Leu Glu Gln Gly Ser Pro
                  50                  55                  60

CCG GAC ATC TCC CCA TAC GAA GTG CCC CCG CTC GCC TCC GAC GAC CCG         361
Pro Asp Ile Ser Pro Tyr Glu Val Pro Pro Leu Ala Ser Asp Asp Pro
                  65                  70                  75
```

```
GCT GGC GCT CAC CTC CAC CAC CAC CTT CCA GCT CAG CTC GGG CTC GCC       409
Ala Gly Ala His Leu His His His Leu Pro Ala Gln Leu Gly Leu Ala
         80                  85                  90

CAT CCA CCT CCC GGA CCT TTC CCG AAT GGA ACC GAG CCT GGG GGC CTG       457
His Pro Pro Pro Gly Pro Phe Pro Asn Gly Thr Glu Pro Gly Gly Leu
 95                 100                 105                 110

GAA GAG CCC AAC CGC GTC CAG CTC CCT TTC CCG TGG ATG AAA TCC ACC       505
Glu Glu Pro Asn Arg Val Gln Leu Pro Phe Pro Trp Met Lys Ser Thr
                115                 120                 125

AAA GCT CAC GCG TGG AAA GGC CAG TGG GCA GGA GGT GCT TAC ACA GCG       553
Lys Ala His Ala Trp Lys Gly Gln Trp Ala Gly Gly Ala Tyr Thr Ala
         130                 135                 140

GAA CCC GAG GAA AAC AAG AGG ACC CGT ACT GCC TAC ACC CGG GCG CAG       601
Glu Pro Glu Glu Asn Lys Arg Thr Arg Thr Ala Tyr Thr Arg Ala Gln
         145                 150                 155

CTG CTG GAG CTG GAG AAG GAA TTC TTA TTT AAC AAA TAC ATC TCC CGG       649
Leu Leu Glu Leu Glu Lys Glu Phe Leu Phe Asn Lys Tyr Ile Ser Arg
        160                 165                 170

CCC CGC CGG GTG GAG CTG GCA GTG ATG TTG AAC TTG ACC GAG AGA CAC       697
Pro Arg Arg Val Glu Leu Ala Val Met Leu Asn Leu Thr Glu Arg His
175                 180                 185                 190

ATC AAA ATC TGG TTC CAA AAC CGT CGC ATG AAG TGG AAA AAA GAG GAA       745
Ile Lys Ile Trp Phe Gln Asn Arg Arg Met Lys Trp Lys Lys Glu Glu
                195                 200                 205

GAT AAG AAA CGT AGT AGC GGG ACC CCG AGT GGG GGC GGT GGG GGC GAA       793
Asp Lys Lys Arg Ser Ser Gly Thr Pro Ser Gly Gly Gly Gly Gly Glu
         210                 215                 220

GAG CCG GAG CAA GAT TGT GCG GTG ACC TCG GGC GAG GAG CTG CTG GCA       841
Glu Pro Glu Gln Asp Cys Ala Val Thr Ser Gly Glu Glu Leu Leu Ala
         225                 230                 235

GTG CCA CCG CTG CCA CCT CCC GGA GGT GCC GTG CCC CCA GGC GTC CCA       889
Val Pro Pro Leu Pro Pro Pro Gly Gly Ala Val Pro Pro Gly Val Pro
         240                 245                 250

GCT GCA GTC CGG GAG GGC CTA CTG CCT TCG GGC CTT AGC GTG TCG CCA       937
Ala Ala Val Arg Glu Gly Leu Leu Pro Ser Gly Leu Ser Val Ser Pro
255                 260                 265                 270

CAG CCC TCC AGC ATC GCG CCA CTG CGA CCG CAG GAA CCC CGG                979
Gln Pro Ser Ser Ile Ala Pro Leu Arg Pro Gln Glu Pro Arg
                275                 280

TGAGGACAGC AGTCTGAGGG TGAGCGGGTC TGGGACCCAG AGTGTGGACG TGGGAGCGGG     1039

CAGCTGGATA AGGGAACTTA ACCTAGGCGT CGCACAAGAA GAAAATTCTT GAGGGCACGA     1099

GAGCCAGTTG GATAGCCGGA GAGATGCTGC GAGCTTCTGA AAAAACAGCC CTGAGCTTCT     1159

GAAAACTTTG AGGCTCGCTC TGATGCCAAG CTAATGGCCA GATCTGCCTC TGAGGACTCT     1219

TTCCTGGGAC CAATTTAGAC AACCTGGGCT CCAAACTGAG GACAATAAAA AGGGTACAAA     1279

CTTGAGCGTT CCAATACGGA CCAGCAGGCG AGAG                                 1313

(2) INFORMATION FOR SEQ ID NO: 2:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO: 2:

Met Asn Ser Glu Glu Gln Tyr Tyr Ala Ala Thr Gln Leu Tyr Lys Asn
 1               5                  10                  15
```

-continued

```
Pro Cys Ala Phe Gln Arg Gly Pro Val Pro Glu Phe Ser Ala Asn Pro
             20                  25                  30

Pro Ala Cys Leu Tyr Met Gly Arg Gln Pro Pro Pro Pro Pro Pro Pro
         35                  40                  45

Gln Phe Thr Ser Ser Leu Gly Ser Leu Glu Gln Gly Ser Pro Pro Asp
     50                  55                  60

Ile Ser Pro Tyr Glu Val Pro Leu Ala Ser Asp Asp Pro Ala Gly
 65                  70                  75                  80

Ala His Leu His His His Leu Pro Ala Gln Leu Gly Leu Ala His Pro
                 85                  90                  95

Pro Pro Gly Pro Phe Pro Asn Gly Thr Glu Pro Gly Gly Leu Glu Glu
             100                 105                 110

Pro Asn Arg Val Gln Leu Pro Phe Pro Trp Met Lys Ser Thr Lys Ala
         115                 120                 125

His Ala Trp Lys Gly Gln Trp Ala Gly Gly Ala Tyr Thr Ala Glu Pro
 130                 135                 140

Glu Glu Asn Lys Arg Thr Arg Thr Ala Tyr Thr Arg Ala Gln Ser Ser
145                 150                 155                 160

Glu Leu Glu Lys Glu Phe Leu Phe Asn Lys Tyr Ile Ser Arg Pro Arg
                 165                 170                 175

Arg Val Glu Leu Ala Val Met Leu Asn Leu Thr Glu Arg His Ile Lys
             180                 185                 190

Ile Trp Phe Gln Asn Arg Arg Met Lys Trp Lys Lys Glu Glu Asp Lys
         195                 200                 205

Lys Arg Ser Ser Gly Thr Pro Ser Gly Gly Gly Gly Gly Glu Glu Pro
 210                 215                 220

Glu Gln Asp Cys Ala Val Thr Ser Gly Glu Glu Leu Leu Ala Val Pro
225                 230                 235                 240

Pro Leu Pro Pro Pro Gly Gly Ala Val Pro Pro Gly Val Pro Ala Ala
                 245                 250                 255

Val Arg Glu Gly Leu Leu Pro Ser Gly Leu Ser Val Ser Pro Gln Pro
             260                 265                 270

Ser Ser Ile Ala Pro Leu Arg Pro Gln Glu Pro Arg
         275                 280
```

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

GCAAGCTTCA TNCKNCKRTT YTGRAACCA                              29

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
GCCCTTAATG GGCCAAACGG CA                                                  22

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

GGGGTTAATG GGCCAAACGG CA                                                  22

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

GCCCTTCCTG GGCCAAACGG CA                                                  22

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

GCCCTTAATC CCCCAAACGG CA                                                  22

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GCCCCTTGTT AATAATCTAA T                                                   21

(2) INFORMATION FOR SEQ ID NO: 9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GCCCTTAATG GGCCAA                                                         16
```

INSULIN PROMOTER FACTOR, AND USES RELATED THERETO

CROSS-REFERENCE TO RELATED APPLICATIONS

This application is a continuation of U.S. application Ser. No. 09/031,898, filed on Feb. 27, 1998, now U.S. Pat. No. 6,197,945, which is a continuation of U.S. application Ser. No. 08/320,148, filed on Oct. 7, 1994, now U.S. Pat. No. 5,849,989, the specifications of which are incorporated herein by reference.

BACKGROUND OF THE INVENTION

Each year, over 728,000 new cases of diabetes are diagnosed and 150,000 Americans die from the disease and its complications; the total yearly cost in the United States is over 20 billion dollars (Langer et al. (1993) *Science* 260:920–926). For instance, diabetes is characterized by pancreatic islet destruction or dysfunction leading to loss of glucose control. Diabetes mellitus is a metabolic disorder defined by the presence of chronically elevated levels of blood glucose (hyperglycemia). Insulin-dependent (Type 1) diabetes mellitus ("IDDM") results from an autoimmune-mediated destruction of the pancreatic β-cells with consequent loss of insulin production, which results in hyperglycemia. Type 1 diabetics require insulin replacement therapy to ensure survival. Non-insulin-dependent (Type 2) diabetes mellitus ("NIDDM") is initially characterized by hyperglycemia in the presence of higher-than-normal levels of plasma insulin (hyperinsulinemia). In Type 2 diabetes, tissue processes which control carbohydrate metabolism are believed to have decreased sensitivity to insulin. Progression of the Type 2 diabetic state is associated with increasing concentrations of blood glucose, and coupled with a relative decrease in the rate of glucose-induced insulin secretion.

The primary aim of treatment in both forms of diabetes mellitus is the same, namely, the reduction of blood glucose levels to as near normal as possible. Treatment of Type 1 diabetes involves administration of replacement doses of insulin. In contrast, treatment of Type 2 diabetes frequently does not require administration of insulin. For example, initial therapy of Type 2 diabetes may be based on diet and lifestyle changes augmented by therapy with oral hypoglycemic agents such as sulfonylurea. Insulin therapy may be required, however, especially in the later stages of the disease, to produce control of hyperglycemia in an attempt to minimize complications of the disease.

More recently, tissue-engineering approaches to treatment have focused on transplanting healthy pancreatic islets, usually encapsulated in a membrane to avoid immune rejection. Three general approaches have been tested in animal models. In the first, a tubular membrane is coiled in a housing that contained islets. The membrane is connected to a polymer graph that in turn connects the device to blood vessels. By manipulation of the membrane permeability, so as to allow freediffusion of glucose and insulin back and forth through the membrane, yet block passage of antibodies and lymphocytes, normoglycemia was maintained in pancreatectomized animals treated with this device (Sullivan et al. (1991) *Science* 252:718).

In a second approach, hollow fibers containing islet cells were immobilized in the polysaccharide alginate. When the device was place intraperitoneally in diabetic animals, blood glucose levels were lowered and good tissue compatibility was observed (Lacey et al. (1991) *Science* 254:1782).

Finally, islets have been placed in microcapsules composed of alginate or polyacrylates. In some cases, animals treated with these microcapsules maintained normoglycemia for over two years (Lim et al. (1980) *Science* 210:908; O'Shea et al. (1984) *Biochim. Biochys. Acta.* 840:133; Sugamori et al. (1989) *Trans. Am. Soc. Artif. Intern. Organs* 35:791; Levesque et al. (1992) *Endocrinology* 130:644; and Lim et al. (1992) *Transplantation* 53:1180).

However, all of these transplantation strategies require a large, reliable source of donor islets.

SUMMARY OF THE INVENTION

The present invention relates to the discovery in eukaryotic cells, particularly mammalian cells, of novel a transcriptional regulatory factor, referred to hereinafter as "Insulin Promoter Factor 1" or "Ipf1".

In general, the invention features an Ipf1 polypeptide, preferably a substantially pure preparation of the polypeptide, or a recombinant Ipf1 polypeptide. In preferred embodiments the polypeptide has a biological activity associated with its binding to Ipf1-responsive elements, such as the P1 insulin promoter site, and with its binding to other transcriptional regulatory proteins. The polypeptide can be identical to the polypeptide shown in SEQ ID NO: 2, or it can merely be homologous to that sequence. For instance, the polypeptide preferably has an amino acid sequence at least 60% homologous to the amino acid sequence in SEQ ID NO: 2, though higher sequence homologies of, for example, 80%, 90% or 95% are also contemplated. The polypeptide of the present invention can comprise the full length protein represented in SEQ ID NO: 2, or it can comprise a fragment of that protein, which fragment may be, for instance, at least 5, 10, 20, 50 or 100 amino acids in length. The fragment can be derived to include, for example, regions of the protein which are likely to be involved in protein-protein interactions with other transcriptional regulatory proteins or which may influence the DNA-binding specficity of the homeodomain of Ipf1 (Glu 146-Ser211) relative to other heterologous homeodomains. For instance, the fragment can include at least 4 amino acid residues between Met1 to Glu145 and/or Ser212 to Arg284, though more preferably includes portions of at least 10, 20, 30 or 50 residues from one or both of those regions. Exemplary fragments include N-terminal fragments within or including Met1 to Glu 145, or C-terminal fragments within or including Glu146 to Arg284.

Moreover, as described below, the Ipf1 polypeptide of the present invention can be either an agonist (e.g. mimics), or alternatively, an antagonist of a biological activity of a naturally occurring form of Ipf1. That is, the polypeptide is an Ipf1 homolog which is able to modulate Ipf1-mediated gene expression (e.g., a gene containing an Ipf1-responsive element) in at least one tissue in which wild-type Ipf1 is expressed, such as in pancreatic tissue, particularly β-islet cells.

In a preferred embodiment, a peptide having at least one biological activity of the subject polypeptide may differ in amino acid sequence from the sequence in SEQ ID NO 2, but such differences result in a modified protein which functions in the same or similar manner as the native Ipf1 or which has the same or similar characteristics of the native Ipf1. Moreover, homologs of the naturally occurring protein are contemplated which are antagonistic of the normal cellular role of the naturally occurring form of Ipf1. For example, the homolog may be capable of interfering with the ability of wild-type Ipf1 to modulate gene expression, e.g. of developmentally or growth regulated genes. Preferred antagonistic forms of an Ipf1 polypeptide either (i) retains the DNA binding ability of authentic Ipf1 but lack the ability to assemble transcriptionally-competent protein complexes, or (ii) lacks DNA binding ability (e.g. to Ipf1-RE2) yet retains the ability to bind to other transcription regulatory complexes normally involving authentic Ipf1.

In yet other preferred embodiments, the Ipf1 polypeptide is a recombinant fusion protein which includes a second polypeptide portion, e.g., a second polypeptide having an amino acid sequence unrelated to Ipf1, e.g. the second polypeptide portion is glutathione-S-transferase, e.g. the second polypeptide portion is a DNA binding domain of a heterologous transcriptional regulatory protein, or the second polypeptide portion is an RNA polymerase activating domain, e.g. the fusion protein is functional in a two-hybrid assay.

Yet another aspect of the present invention concerns an immunogen comprising an Ipf1 peptide in an immunogenic preparation, the immunogen being capable of eliciting an immune response specific for said Ipf1 polypeptide. The response can be in the form of a humoral response, e.g. an antibody response or a cellular response. In preferred embodiments, the immunogen comprising an antigenic determinant, e.g. a unique determinant, from a protein represented by SEQ ID NO: 2.

A still further aspect of the present invention features an antibody preparation specifically reactive with an epitope of an Ipf1 polypeptide, such as an Ipf1 immunogen.

Another aspect of the present invention provides a substantially isolated nucleic acid having a nucleotide sequence which encodes an Ipf1 polypeptide. In preferred embodiments: the encoded polypeptide specifically binds an Ipf1-responsive element, and/or is able to either agonize or antagonize assembly of Ipf1-dependent transcriptional protein complexes. The coding sequence of the nucleic acid can comprise an Ipf1-encoding sequence which can be identical to the cDNA shown in SEQ ID NO: 1, or it can merely be homologous to that sequence. For instance, the Ipf1-encoding sequence preferably has a sequence at least 60% homologous to the nucleotide sequence in SEQ ID NO: 1, though higher sequence homologies of, for example, 80%, 90% or 95% are also contemplated. The polypeptide encoded by the nucleic acid can comprise the nucleotide sequence represented in SEQ ID NO: 1 which encodes the full length protein, or it can comprise a fragment of that nucleic acid, which fragment may be, for instance, a fragment of the full length Ipf1 protein which is, for example, at least 5, 10, 20, 50 or 100 amino acids in length. The polypeptide encoded by the nucleic acid can be either an agonist (e.g. mimics), or alternatively, an antagonist of a biological activity of a naturally occurring form of the Ipf1 protein, e.g., the polypeptide is able to modulate Ipf1-dependent gene expression in at least one tissue in which the Ipf1 protein is expressed, such as in pancreatic tissue.

Furthermore, in certain preferred embodiments, the subject Ipf1 nucleic acid will include a transcriptional regulatory sequence, e.g. at least one of a transcriptional promoter or transcriptional enhancer sequence, which regulatory sequence is operably linked to the Ipf1 gene sequence. Such regulatory sequences can be used in to render the Ipf1 gene sequence suitable for use as an expression vector.

In yet a further preferred embodiment, the nucleic acid hybridizes under stringent conditions to a nucleic acid probe corresponding to at least 12 consecutive nucleotides of SEQ ID NO: 1; preferably to at least 20 consecutive nucleotides of SEQ ID NO: 1; more preferably to at least 40 consecutive nucleotides of SEQ ID NO: 1.

The invention also features transgenic non-human animals, e.g. mice, rats, rabbits or pigs, having a transgene, e.g., animals which include (and preferably express) a heterologous form of the Ipf1 genes described herein, e.g. a gene derived from humans, or which misexpress an endogenous Ipf1 gene, e.g., an animal in which expression of the subject Ipf1 protein is disrupted. Such a transgenic animal can serve as an animal model for studying cellular disorders comprising mutated or mis-expressed Ipf1 alleles or for use in drug screening.

The invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of one of SEQ ID NO: 1, or naturally occurring mutants thereof. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying β-islet cells including abnormal β-cells, as well as abnormal pancreatic tissues. For instance, the probe can be employed for detecting, in a sample of cells isolated from a patient, a level of a nucleic acid encoding the subject Ipf1 protein or mutated forms thereof; e.g. measuring the Ipf1 mRNA level in a cell, or determining whether the genomic Ipf1 gene has been mutated or deleted. Preferably, the oligonucleotide is at least 10 nucleotides in length, though primers of 20, 30, 50, 100, or 150 nucleotides in length are also contemplated.

In yet another aspect, the invention provides an assay for screening test compounds for an inhibitor, or alternatively, a potentiator, of an interaction between an Ipf1 and an Ipf1-responsive element (such as a P1 promoter), or with other transcriptional regulatory proteins. An exemplary method includes the steps of (i) combining an Ipf1 protein, a test compound, and an Ipf1-target molecule, under conditions wherein, but for the test compound, the Ipf1 protein and the Ipf1-target molecule are able to interact; and (ii) detecting the formation of a complex which includes the Ipf1 protein and the target molecule. A statistically significant change, such as a decrease, in the formation of the complex in the presence of a test compound (relative to what is seen in the absence of the test compound) is indicative of a modulation, e.g., inhibition, of the interaction between Ipf1 and the target molecule. In preferred embodiments, the target molecule is an Ipf1-responsive element, e.g., a nucleic acid comprising an Ipf1 binding sequence, such as an insulin P1 promoter sequence. In alternative embodiments, the target molecule is a protein which binds Ipf1, such as a protein involved in forming transcriptional regulatory complexes with Ipf1. Moreover, primary screens are provided in which the target molecule and Ipf1 are combined in a cell-free system and contacted with the test compound; i.e. the cell-free system is selected from a group consisting of a cell lysate and a reconstituted protein:DNA or protein:protein mixture. Alternatively, the target molecule and Ipf1 protein are simultaneously provided in a cell, and the cell is contacted with the test compound. For example, where the target molecule is a nucleic acid comprising an Ipf1-responsive element, the expression of a marker gene controlled by the Ipf1-responsive element is detected.

The present invention also provides a method for treating an animal, including a human, having a disorder characterized by a loss of, or abnormal control of, wild-type function of Ipf1, comprising administering an effective amount of an Ipf1 agonist. In one embodiment, the method comprises administering a nucleic acid construct encoding a polypeptide represented in SEQ ID NO: 2, under conditions wherein the construct is incorporated by cells deficient in insulin production, and under conditions wherein the recombinant gene is expressed, e.g. by gene therapy techniques. In other embodiments, the action of a naturally-occurring Ipf1 protein is antagonized by therapeutic expression of an Ipf1 homolog which is an antagonistic of, for example, assembly of functional Ipf1 transcriptional regulatory complexes, or by delivery of an antisense nucleic acid molecule which inhibits IPF transcriptional regulation. Such techniques can likewise be used to treat a disorder characterized by abherent or unwanted expression of a gene regulated by an Ipf1-RE, such as an insulin gene.

Another aspect of the present invention provides a method of determining if a subject, e.g. a human patient, is at risk for a disorder characterized by unwanted cell proliferation or differentiation. The method includes detecting, in a tissue of the subject, the presence or absence of a genetic lesion characterized by at least one of (i) a mutation of a gene encoding a protein represented by SEQ ID NO: 2, or a homolog thereof; (ii) the mis-expression of a gene encoding a protein represented by SEQ ID NO: 2; or (iii) the mis-incorporation of Ipf1 in a transcriptional regulatory complex. In preferred embodiments: detecting the genetic lesion includes ascertaining the existence of at least one of: a deletion of one or more nucleotides from the Ipf1 gene; an addition of one or more nucleotides to the gene, an substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (i) providing a probe/primer including an oligonucleotide containing a region of nucleotide sequence which hybridizes to a sense or antisense sequence of SEQ ID NO: 1, or naturally occurring mutants thereof or 5' or 3' flanking sequences naturally associated with the Ipf1 gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the Ipf1 gene and, optionally, of the flanking nucleic acid sequences. For instance, the probe/primer can be employed in a polymerase chain reaction (PCR) or in a ligation chain reaction (LCR). In alternate embodiments, the level of Ipf1 protein and/or its participation in complexes is detected in an immunoassay using an antibody which is specifically immunoreactive with a protein represented by SEQ ID NO: 2.

The invention also features transgenic non-human animals, e.g. mice, rats, rabbits or pigs, harboring in one or more of its cells an Ipf1-encoding transgene. In preferred embodiments, the transgene is expressed, causing Ipf1-dependent gene transcription where the transgene encodes an agonistic form of the protein, or disruption of Ipf1-induced expression where the transgene encodes an antagonistic form of the protein. Such transgenic animals can serve as models for studying cellular and tissue disorders comprising mutated or mis-expressed Ipf1 alleles, as well as for studying the physiological role of Ipf1 in proliferation, differentiation and maintenance of tissues in vivo in both adult and embryonic systems. Furthermore, inhibition of Ipf1 expression in certain cells, such as β-cells, can be used to unravel the effects of various autocrine and paracrine functions of pancreatic hormones, and can be used in drug screening assays designed to detect modulators of these other factors.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleolide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986). Other references include Ohlsson et al. (1993) *EMBO J* 12:4251–4259; Ohlsson et al. (1 991) *Mol Endo* 5:897–904; Walker et al. (1 983) *Nature* 306:557–561; Leonard et al. (1993) *Mol Endo* 7:1275–1283; Miller et al. (1994) *EMBO J* 13:1145–1156; and Harrison et al. (1994) *J Biol Chem* 269:19968–19975, all of which are incorporated by reference herein.

Other features and advantages of the invention will be apparent from the following detailed description, and from the claims.

DESCRIPTION OF THE DRAWINGS

(FIG. 1A) Mutation of the P1 promoter site results in a decreased activity for the rat insulin I 5' flank and the stimulation of the activity of the 5' flank as a result of Ipf1 expression is critically dependent on an intact P1 site. RSV and RSVI/Ipf1 recombinant expression vectors were co-transfected with the Tk-CAT, Ins-CAT and P1mut #2/Ins-CAT reporter genes into βTC1 cells using an internal control β-gal plasmid as described previously (Walker et al. (1983) *Nature* 306:557–581). (FIG. 1B) Multimers of the P1 site in front of a reporter gene is specifically trans-activated by the expression of the Ipf1 gene in heterologous cells. RSV, RSV-Ipf1 and RSV-Isl1 recombinant expression vectors were co-transfected with the β-globin-CAT and 5×P1 β-globin-CAT construct in CHO cells. (FIG. 1C) Overexpression of the Ipf1 gene in βTC1 cells results in a further up-regulation of the activity of the P1 element. RSV and RSV-Ipf1 recombinant expression vectors were co-transfected with the β-globin-CAT and 5×P1 β-globin-CAT construct in βTC1 cells. The numbers given are normalized to the internal control and represent the mean of at least five independent transfection experiments. In all cases, the standard error of the mean was <15% of this value.

DETAILED DESCRIPTION OF THE INVENTION

Figure 1A:
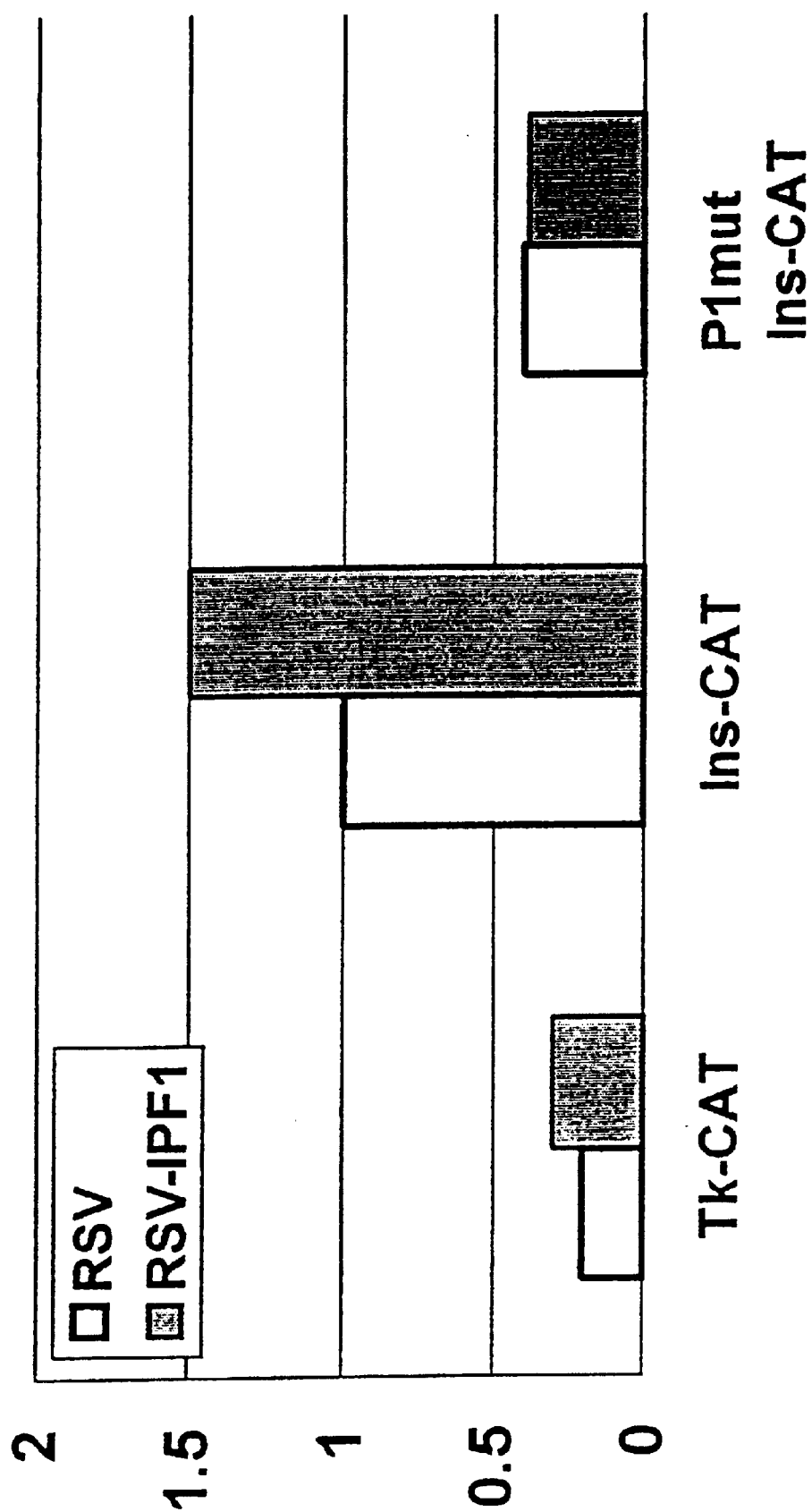
FIGS. 1A, 1B and 1C illustrate the results of expression of the Ipf1 gene in both β-cells and non-β-cells transactivates a reporter construct via the P1 site.

The endocrine pancreas of mammals is composed of several thousand islets of Langherhans. Each individual islet contains four hormone-producing cell types in a characteristic proportion and distribution, with the different hormone-producing cells appearing sequentially during embryo genesis (Pictet et al. (1972) in Steiner, D. F. and Frenkel, M. (EDS), *Handbook of Physiology*, Series 7, *American Physiology Society*, Washington, D.C., pp. 25–66; Yoshinari et al. (1992) *Anat. Embryol.* 165:63–70; Titelman et al. (1987) *Dev. Biol.* 121:454–466; Herrera et al. (1991) *Development* 113:1257–1265; Gitts et al. (1992) *PNAS* 89:1128–1132). Although the precise lineage relationship between the different islet cells is not known, co-expression of different hormone genes during normal pancreas development and in cloned cell-lines derived from islet cell tumors suggests a common precursor for the pancreatic endocrine cells (Medsen et al. (1986) *J Cell Biol.* 103:2025–2034; Alpert et al. (1988) *Cell* 53:295–308; and Herrera et al. Supra). These observations have suggested that terminal differentiation, restricting the expression of the hormone genes to the individual endocrine cell-type, occurs relatively late in the ontogeny of the endocrine pancreas.

For some of these hormone genes it has been possible to identify the cis- and trans-acting elements that regulate the islet-specific expression of the genes. For instance, the insulin-1 gene contains approximately 350 basepairs of 5' flanking DNA (e.g., the "insulin transcriptional regulatory sequence") which is sufficient for selective, β-cell specific expression both in cell lines and in transgenic animals (Walker et al. (1983) *Nature* 306:557–581; and Alpert et al., supra), with both a strong β-cell enhancer and a promoter element contained within these 350 basepairs (Edlund et al. (1983) *Science* 230:912–916; and Karlson et al. (1987) *PNAS* 84:8819–8823).

This invention, as described below, derives in part from the cloning of a mamalian transcriptional regulatory protein which binds to and activates transcription from the insulin transcriptional regulatory sequence. This transcriptional regulatory factor, referred to hereinafter as "Insulin Promoter Factor 1" or "Ipf1" is apparently part of the mechanism involved in developmental coordination of endoderm differentiation, particularly of the pancreas and other tissues derived from the primative gut. For instance, as described in the appended examples, analysis of Ipf1 expression patterns demonstrate that Ipf1 expression occurs in the developing foregut endoderm when this tissue commits to a pancreatic fate. Moreover, transgenic animals in which Ipf1 expression is disrupted selectively lack a pancreas. These findings show that Ipf1 is needed for the formation of the pancreas, and strongly implicates Ipf1 function in the determination and/or maintenance of the pancreatic identity of common precursor cells, and/or in the regulation of their propagation. Ipf1-mediated gene expression is presumably important in the pathogenesis of diabetes and other abnormal glycemic disease states, and may also be of significance in the progression and pathology of other proliferative or differentiative disorders. Consequently, the interaction of Ipf1 with Ipf1-responsive elements, as well as with other regulatory proteins, may be significant in the modulation of cellular homeostasis, in the control of organogenesis, and/or in the maintenance of differentiated tissues, as well as in the development of tissue failure and neoplastic disorders.

Accordingly, certain aspects of the present invention relate to diagnostic and therapeutic assays and reagents for detecting and treating disorders involving abherent assembly of Ipf1 transcriptional complexes. Moreover, drug discovery assays are provided for identifying agents which can modulate the binding of Ipf1 with other transcriptional regulatory proteins or with Ipf1 responsive elements. Such agents can be useful therapeutically to alter the growth and/or differentiation of pancreatic cell. Other aspects of the invention are described below or will be apparent to those skilled in the art in light of the present disclosure.

For convenience, certain terms employed in the specification, examples, and appended claims are collected here.

As used herein, the term "gene" or "recombinant gene" refers to a nucleic acid comprising an open reading frame encoding an insulin promoter factor of the present invention, including both exon and (optionally) intron sequences. A "recombinant gene" refers to nucleic acid encoding Ipf1 and comprising Ipf1-encoding exon sequences, though it may optionally include intron sequences which are either derived from a chromosomal Ipf1 gene or from an unrelated chromosomal gene. An exemplary Ipf1 recombinant gene is represented by any one of SEQ ID NO: 1. The term "intron" refers to a DNA sequence present in a given Ipf1 gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of Ipf1, or where anti-sense expression occurs, from the transferred gene, the expression of a naturally-occurring form of Ipf1 is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto. "Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant Ipf1 gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of a naturally-occurring form of Ipf1.

As used herein, the term "Ipf1-responsive element" or "Ipf1-RE" refers to a transcriptional regulatory sequence which controls expression of a gene in an Ipf1-dependent manner. That is, the Ipf1-RE has a nucleotide sequence which is specifically bound by an Ipf1 protein, and the binding of Ipf1 regulates expression of a gene operably linked to the Ipf1-RE. An exemplary Ipf1-RE is the 5' flanking transcriptional regulation DNA of the insulin I gene, particularly the P1 promoter site (SEQ ID NO: 9) 5'-GCCCTTAATGGGCCAA, or its core sequence TAATGGG.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g. renal cells, or cells of a neural origin, e.g. neuronal cells. The term also covers so-called "leaky" promoters, which regulate expression of a selected DNA primarily in one tissue, but cause expression in other tissues as well.

As used herein, a "transgenic animal" is any animal, preferably a non-human mammal, bird or an amphibian, in which one or more of the cells of the animal contain heterologous nucleic acid introduced by way of human intervention, such as by trangenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of Ipf1, e.g. either agonistic or antagonistic forms. However, transgenic animals in which the recombinant Ipf1 gene is silent are also contemplated, as for example, the FLP or CRE recombinase dependent constructs described below. Transgenic animals also include both constitutive and conditional "knock out" animals. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that the recombinant Ipf1 gene is present and/or expressed in some tissues but not others.

As used herein, the term "transgene" means a nucleic acid sequence (encoding, e.g., a Ipf1), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout or other loss-of-function mutation). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an Ipf1 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity. "Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. "Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding an Ipf1 polypeptide with a second amino acid sequence defining a domain foreign to and not substantially homologous with any domain of the subject Ipf1. A chimeric protein may present a foreign domain which is found (albeit in a different protein) in an organism which also expresses the first protein, or it may be an "interspecies", "intergenic", etc. fusion of protein structures expressed by different kinds of organisms.

The term "evolutionarily related to", with respect to nucleic acid sequences encoding Ipf1, refers to nucleic acid sequences which have arisen naturally in an organism, including naturally occurring mutants. The term also refers to nucleic acid sequences which, while derived from a naturally occurring Ipf1, have been altered by mutagenesis, as for example, combinatorial mutagenesis described below, yet still encode polypeptides which have at least one activity of a Ipf1.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject Ipf1 preferably includes no more than 10 kilobases (kb) of nucleic acid sequence which naturally immediately flanks that particular Ipf1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to an isolated nucleic acid comprising the nucleotide sequence encoding an Ipf1 polypeptide, and/or equivalents of such nucleic acids. The term nucleic acid as used herein is intended to include fragments and equivalents. The term equivalent is understood to include nucleotide sequences encoding functionally equivalent Ipf1 molecules or functionally equivalent polypeptides which, for example, retain the ability to bind to other transcriptional regulatory proteins or to transcriptional regulatory sequences of, for example, an insulin gene. Equivalent nucleotide sequences will include sequences that differ by one or more nucleotide substitutions, additions or deletions, such as allelic variants; and will, therefore, include sequences that differ from the nucleotide sequence of Ipf1 shown in SEQ ID NO: 1 due to the degeneracy of the genetic code. Equivalents will also include nucleotide sequences which hybridize under stringent conditions (i.e., equivalent to about 20–27° C. below the melting temperature ($T_m$) of the DNA duplex formed in about 1M salt) to the nucleotide sequence represented in SEQ ID NO: 1. In one embodiment, equivalents will further include nucleic acid sequences derived from or otherwise related to, the nucleotide sequence shown SEQ ID NO: 1.

For example, it will be generally appreciated that, under certain circumstances, it may be advantageous to provide homologs of the subject Ipf1 protein which, while not identical to SEQ ID NO.: 2, function as an Ipf1 agonist or an Ipf1 antagonist, in order to promote or inhibit the biological activities of the naturally-occurring form of the protein. For instance, antagonistic homologs can be generated which interfere with the ability of wild-type ("authentic") Ipf1 to form transcriptional activating complexes at Ipf1-responsive elements. As described below, an antagonistic Ipf1 homolog, such as a truncation mutant which retains DNA-binding activity yet is transcriptionally defective, can be used in the treatment of, for example, hyperinsulinemia.

A polypeptide is considered to possess a biological activity of Ipf1 if the polypeptide has one or more of the following properties: the ability to modulate at least one of proliferation, differentiation or survival of a cell which expresses a gene that is transcriptionally regulated by an Ipf1-RE; the ability to modulate gene expression of a gene that is transcriptionally regulated by an Ipf1-RE, e.g. of a developmentally or growth regulated gene, e.g. of an insulin gene; the ability to modulate gene expression in pancreatic tissue, e.g. in the ability to bind to the ability agonize or antagonize assembly of Ipf1-containing transcriptional protein complexes. An Ipf1 polypeptide may additionally be characterized by the ability to modulate differentiation of endodermally-derived tissue, such as tissue derived from the primitive gut, e.g. pancreatic tissue, e.g. β-cells. A protein also has Ipf1 biological activity if it is a specific agonist or antagonist of one of the above recited properties.

Preferred nucleic acids encode an Ipf1 polypeptide comprising an amino acid sequence at least 60% homologous, more preferably 70% homologous and most preferably 80% homologous with an amino acid sequence shown in one of SEQ ID NO: 2. Nucleic acids which encode polypeptides that retain an activity of Ipf1 and having at least about 90%, more preferably at least about 95%, and most preferably at least about 98–99% homology with a sequence shown in one of SEQ ID NO: 2 are also within the scope of the invention, as of course are proteins which are identical to the aforementioned sequence listings. In one embodiment, the nucleic acid is a cDNA encoding a peptide having at least one activity of the subject Ipf1 protein. Preferably, the nucleic acid is a cDNA molecule comprising at least a portion of the nucleotide sequence represented in one of SEQ ID NO: 1. A preferred portion of these cDNA molecules includes the coding region of the gene.

Another aspect of the invention provides a nucleic acid which hybridizes under high or low stringency conditions to a DNA or RNA which encodes a peptide having all or a portion of the amino acid sequence shown in SEQ ID NO: 2. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids which have a sequence that differ from the nucleotide sequence shown in SEQ ID NO: 1 due to degeneracy in the genetic code are also within the scope of the invention. Such nucleic acids encode functionally equivalent peptides (i.e., a peptide having a biological activity of a Ipf1) but that differ in sequence from said sequence listings due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of Ipf1 polypeptide. However, it is expected that DNA sequence polymorphisms that do lead to changes in the amino acid sequences of the subject Ipf1 will exist among vertebrates. One skilled in the art will appreciate that these variations in one or more nucleotides (up to about 3–5% of the nucleotides) of the nucleic acids encoding Ipf1 polypeptides Ipf1 may exist among individuals of a given species due to natural allelic variation. Any and all such nucleotide variations and resulting amino acid polymorphisms are within the scope of this invention.

Fragments of the nucleic acid encoding the subject Ipf1 are also within the scope of the invention. As used herein, a fragment encoding the active portion of a Ipf1 refers to a nucleic acid having fewer nucleotides than the nucleotide sequence encoding the entire amino acid sequence of Ipf1 but which nevertheless encodes a peptide which is either an agonist or antagonist of authentic Ipf1, e.g. the fragment retains the ability to bind to an insulin promoter. Nucleic acid fragments within the scope of the present invention include those capable of hybridizing under high or low stringency conditions with nucleic acids from other species for use in screening protocols to detect Ipf1 homologs, including alternate isoforms, e.g. mRNA splicing variants. Nucleic acids within the scope of the invention may also contain linker sequences, modified restriction endonuclease sites and other sequences useful for molecular cloning, expression or purification of recombinant forms of the subject Ipf1 protein.

As indicated by the examples set out below, a nucleic acid encoding Ipf1 or a homologous gene thereof may be obtained from mRNA present in any of a number of eukaryotic cells. It should also be possible to obtain nucleic acids encoding Ipf1 from genomic DNA obtained from both adults and embryos. For example, a gene encoding Ipf1 can be cloned from either a cDNA or a genomic library in accordance with protocols herein described, as well as those generally known to persons skilled in the art. A cDNA encoding a Ipf1 can be obtained by isolating total mRNA from a cell, e.g. a mammalian cell, e.g. a human cell. Double stranded cDNAs can then be prepared from the total mRNA, and subsequently inserted into a suitable plasmid or bacteriophage vector using any one of a number of known techniques. The gene encoding the Ipf1 can also be cloned using established polymerase chain reaction techniques in accordance with the nucleotide sequence information provided by the invention. The nucleic acid of the invention can be DNA or RNA. A preferred nucleic acid is a cDNA represented by the sequence shown in SEQ ID NO: 1.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding an Ipf1 protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an Ipf1 protein. Alternatively, the antisense construct can be an oligonucleotide probe which is generated ex vivo and which, when introduced into the cell causes inhibition of expression by hybridizing with the mRNA and/or genomic sequences of an Ipf1 gene. Such oligonucleotide probes are preferably modified oligonucleotides which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa., and may include both human and vetinary formulations. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of Ipf1 (by inhibiting its expression), can be used in the manipulation of tissue, e.g. tissue differentiation, both in vivo and in ex vivo tissue cultures, as well as in the treatment of hyperinsulinenemia, such as during various stages of non-insulin dependent 2) diabetes mellitus.

This invention also provides expression vectors containing a nucleic acid encoding an Ipf1 polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a recombinant Ipf1 polypeptide. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences—sequences that control the expression of a DNA sequence when operatively linked to it may be used in these vectors to express DNA sequences encoding the Ipf1 proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a polypeptide which mimics or otherwise agonizes the action of Ipf1, or alternatively, which encodes a polypeptide that antagonizes the action of an authentic Ipf1. Such expression vectors can be used to transfect cells and thereby produce and (optionally) purify proteins, including fusion proteins or peptides, encoded by nucleic acids as described herein.

Moreover, the gene constructs of the present invention can also be used as a part of a gene therapy protocol to deliver nucleic acids encoding either an agonistic or antagonistic form of the subject Ipf1 proteins. Thus, another aspect of the invention features expression vectors for in vivo transfection and expression of an Ipf1 polypeptide in particular cell types so as to reconstitute the function of, or alternatively, abrogate the function of Ipf1 in a cell in which that protein or other transcriptional regulatory proteins to which it binds are misexpressed. For example, gene therapy can be used to deliver a gene encoding an Ipf1 protein which promotes insulin expression, such as in the generation of β-cells.

Expression constructs of the subject Ipf1 proteins, and mutants thereof, may be administered in any biologically effective carrier, e.g. any formulation or composition capable of effectively delivering the Ipf1 gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of Ipf1 expression are also useful for in vitro transduction of cells, such as for use in a diagnostic assays.

A preferred approach for in vivo introduction of nucleic acid into a cell is by use of a viral vector containing nucleic acid, e.g. a cDNA, encoding the Ipf1 polypeptide or homolog thereof. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up the vector.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood76:271). Thus, recombinant retrovirus can be constructed in which part of the retroviral coding sequence (gag, pol, env) has been replaced by nucleic acid encoding an Ipf1 polypeptide, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Nail. Acad. Sci. USA* 85:6460–6464; Wilson et al. (1988) *Proc. Nail. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J Immunol*. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) PNAS 86:9079–9083; Julan et al. (1992) *J Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety receptor-ligand drug, as well as by generating fusion proteins (e.g. single-chain antibody/env fusion proteins). For example, agents which bind to β-cell receptors (either ligand or antibody) can be used to enhance infection of β-cells. To illustrate, derivatization of the viral particle with ligands for at least one of the gluca gon-like peptide receptor (GLP), the sulfonylurea receptor, the galanin receptor, or antibodies against β-cell antigens, such as GAD65. This technique, while useful to limit or otherwise direct the infection to pancreatic tissue, can also be used to convert an ecotropic vector in to an amphotropic vector.

Another viral gene delivery system useful in the present invention utilitizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J ViroL* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted Ipf1 gene can be under control of, for example, the E1A promoter, the major late promoter (MLP) and associated leader sequences, the E3 promoter, or exogenously added promoter sequences.

Yet another viral vector system useful for delivery of the subject Ipf1 genes is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J Virol.* 63:3822–3828; and McLaughlin et al. (1989) *J Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce Ipf1 genes into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J Virol.* 51:611–619; and Flotte et al. (1993). *J Biol. Chem.* 268:3781–3790).

In addition to viral transfer methods, such as those illustrated above, non-viral methods can also be employed to cause expression of an Ipf1 polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject Ipf1 gene by the targeted cell. Exemplary gene delivery systems of this type include liposomal derived systems, poly-lysine conjugates, and artificial viral envelopes.

In a representative embodiment, a therapeutic Ipf1 gene can be entrapped in liposomes bearing positive charges on their surface (e.g., lipofectins) and (optionally) which are tagged with antibodies or ligands for pancreatic cell surface antigens (Mizuno et al. (1992) *No Shinkei Geka* 20:547–551; PCT publication WO91/06309; Japanese patent application 1047381; and European patent publication EP-A-43075). For example, lipofection of β-cells can be carried out using liposomes tagged with monoclonal antibodies against, for example, the GAD65 antigen, or any other cell surface antigen present on these pancreatic cells. Alternatively, liposomes can be derivatize with such receptor ligands glimepiride, glibenclamide or other sulfonylurea drug.

In clinical settings, the gene delivery systems for therapeutic Ipf1 genes can be introduced into a patient (or non-human animal) by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced into the pancreas by catheter (see U.S. Pat. No. 5,328,470), by stereotactic injection (e.g. Chen et al. (1994) *PNAS* 91: 3054–3057), or by electroporation during a partial pancreatectomy (Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

There are a wide variety of pathological cell proliferative and differentiative conditions for which the Ipf1 gene constructs of the present invention may provide therapeutic benefits, with the general strategy being, for example, the correction of abherent insulin expression, or modulation of differentiative events mediated by Ipf1, such as may be influenced by transcriptional regulatory sequences of other genes with which the subject Ipf1 interact. More generally, however, the present invention relates to a method of inducing and/or maintaining a differentiated state, enhancing survival and/or affecting proliferation of a cell in which Ipf1 responsive genes are expressed, by contacting the cell with an agent which modulates the function (as an agonist or an antagonist) of Ipf1. For instance, it is contemplated by the invention that, in light of the apparent involvement of Ipf1 in the formation of ordered spatial arrangements of pancreatic tissues, the subject method could be used to generate and/or maintain such tissue both in vitro and in vivo. For instance, modulation of the function of Ipf1 can be employed in both cell culture and therapeutic methods involving generation and maintenance β-cells and possibly also for non-pancreatic tissue, such as in controlling the development and maintenance of tissue from the digestive tract, spleen, lungs, and other organs which derive from the primitive gut. The agent can be, as appropriate, any of the preparations described herein, including gene therapy constructs, antisense molecules, peptidomimetics or other agents identified in the drug screening assays provided herein.

In an exemplary embodiment, the present method can be used in the treatment of hyperplastic and neoplastic disorders effecting pancreatic tissue, particularly those characterized by abherent proliferation of β-cells, or mis-expression of Ipf1 or other proteins involved in regulatory complexes involving Ipf1. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. Stimulation of Ipf1-mediated expression of insulin, such as by overexpression of exogenous Ipf1 in β-cells, can be used to increase the insulin production of normal β-cells in the tissue, as well as enhznce regeneration of the tissue after anti-tumor therapy.

In contrast, other pancreatic tumors, such as islet tumors (e.g., insulinomas), are marked by overproduction of insulin (i.e., hyperinsulinemia), which can cause hypoglycemic conditions in a patient. Indeed, hypoglycemia can result from any one of a number of different disorders which result in raised plasma insulin levels, including other β-cell abnormalities, as well as endocrinopathies, sepsis (including malaria), congestive cardiac failure, hepatic and renal insufficiencies, various genetic abnormalities of metabolism, and exogenous toxins (such as alcohol). According to the present invention, hypoglycemic conditions can be treated by administering therapeutic amounts of an agent able to antagonize Ipf1-mediated expression of insulin. Depending on the desired half-life of the effects of the treatment, such agents can range from peptidomimetic and other small molecule inhibitors of Ipf1 function, to antisense constructs, to transient or long-term gene therapy regimens.

Furthermore, the subject method can be used as part of treatments for various forms of diabetes, as well as other pathologies resulting from direct physical/chemical damage to β-cells which result in necrosis and loss of functional islet tissue. In diabetes mellitus, insulin secretion is either completely absent (IDDM) or inappropriately regulated (NIDDM). However, each is characterized by the presence of chronically elevated levels of blood glucose (hyperglycemia). The primary aim of treatment in both forms is the same, namely, the reduction of blood glucose levels to as near as normal as possible. For example, treatment of IDDM typically involves administration of replacement doses of insulin. In constrast, initial therapy for NIDDM may be based in part on therapies which include administration of hypoglycemic agents such as sulfonylurea, though insulin treatment in later stages of the disease may be required to effect normoglycemia. Accordingly, the present method can provide a means for controlling diabetogenous glycemic levels, by administeration of an Ipf1 agonist (e.g. a hyperglycemic agent) as, for example, by causing recombinant expression of a wild-type form of the protein in β-islet cells of the patient, or alternatively, admininstration of an Ipf1 antagonist (e.g. a hypoglycemic agent) such as a molecule which inhibits response element binding and/or activation of insulin gene transcription by Ipf1 or Ipf1-containing complexes.

Moreover, manipulation of Ipf1-mediated gene expression, such as of the insulin gene, may be useful for reshaping/repairing pancreatic tissue both in vivo and in vitro. In one embodiment, the present invention makes use of the apparent involvement of the subject Ipf1 protein in regulating the development of pancreatic tissue responsible for formation of β-cells, e.g. induction of β-cell differentiation from ductal tissue, as well as other tissue from the lungs and other organs which derive from the primitive gut. For example, therapeutic compositions for modulating the role of Ipf1 in tissue differentiation can be utilized to preserve any β-cells that have not been destroyed by diabetic or tumorogenic causes, as well as to induce regeneration of β-cells so as to increase the islet mass. In general, the subject method can be employed therapeutically to regulate the pancreas after physical, chemical or pathological insult.

In yet another embodiment, the subject method can be applied to to cell culture techniques, and in particular, may be employed to enhance the initial generation of prosthetic pancreatic tissue devices. Manipulation of Ipf1 function, for example, by altering the ability of the protein to transactivate Ipf1 responsive genes, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactive all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embyonal traits in mature β-cells can be observed. By utilizing agents which potentiate the action of Ipf1, such as Ipf1 gene expression vectors. . .

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of Ipf1 function to affect tissue differentiation can be utilized as a means of maintaining graft viability.

As set out above, the present method is also applicable to cell culture techniques. In one embodiment, manipulation of differentiative states of renal or urogenital tissue can be performed in order to provide cells lines, especially primary cell lines, which maintain a particular phenotype, such as cell lines which are derived from uteric bud cells. In another embodiment, the differentiation of gondal tissue in culture, such as Sertoli cells, can be controlled by manipulation of the subject Ipf1.

Conversely, control of one or more of the functions of Ipf1 can be accomplished to inhibit differentiation along certain pathways, particularly where uncommitted pluripotent stem cells are being cultured, so that cultures can be manipulated along alternate developmental pathways. Accordingly, manipulation of Ipf1 function by the present method to culture stem cells can be to induce differentiation of the uncommitted progenitor and thereby give rise to a committed progenitor cell, or to cause further restriction of the developmental fate of a committed progenitor cell towards becoming a terminally-differentiated neuronal cell. Such neuronal cultures can be used as convenient assay systems as well as sources of implantable cells for therapeutic treatments.

The manipulation of the biological function of the subject Ipf1 can be carried out using solely such reagents as described herein, or in combination with treatment with neurotrophic factors which act to more particularly enhance a specific differentiation fate of the neuronal progenitor cell. In the later instance, manipulation of Ipf1 involvement in cell regulation might be viewed as ensuring that the treated cell is poised along a certain developmental pathway so as to be properly induced upon contact with a neurotrophic factor.

Another aspect of the present invention concerns recombinant forms of the subject Ipf1 polypeptides. The term "recombinant protein" refers to a protein of the present invention which is produced by recombinant DNA techniques, wherein generally DNA encoding the subject Ipf1 protein is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native Ipf1, or an amino acid sequence similar thereto which is generated by mutations including substitutions and deletions (including truncation). Recombinant proteins preferred by the present invention, in addition to native Ipf1, are at least 60% homologous, more preferably 70% homologous and most preferably 80% homologous with an amino acid sequence shown in one of SEQ ID NO: 2. Polypeptides having an activity of the subject Ipf1 polypeptides (i.e. either agonistic or antagonistic of the naturally-occurring protein) and having at least about 90%, more preferably at least about 95%, and most preferably at least about 98–99% homology with a sequence of either in SEQ ID NO: 2 are also within the scope of the invention.

The present invention further pertains to recombinant forms of the subject Ipf1 which are evolutionarily related to the Ipf1 protein represented in SEQ ID NO: 2, that is, not identical, yet which are capable of functioning as an agonist or an antagonist of at least one biological activity of that protein. The term "evolutionarily related to", with respect to amino acid sequences of recombinant Ipf1, refers to proteins which have amino acid sequences that have arisen naturally, as well as to mutational variants which are derived, for example, by recombinant mutagenesis. Such evolutionarily derived Ipf1 preferred by the present invention are at least 60% homologous, more preferably 70% homologous and most preferably 80% homologous with the amino acid sequence shown in SEQ ID NO: 2. Polypeptides having at least about 90%, more preferably at least about 95%, and most preferably at least about 98–99% homology with a sequence shown in SEQ ID NO: 2 are also within the scope of the invention.

The present invention further pertains to methods of producing the subject Ipf1 polypeptides. For example, a host cell transfected with a nucleic acid vector directing expression of Ipf1 can be cultured under appropriate conditions to allow expression of the polypeptide to occur. The polypeptide may be secreted, e.g. with the use of an exogenous signal sequence, and isolated from a mixture of cells and medium containing the recombinant protein. Alternatively, the peptide may be retained cytoplasmically, as the naturally occurring form of the protein is believed to be, and the cells harvested, lysed and the protein isolated. A cell culture includes host cells, media and other byproducts. Suitable media for cell culture are well known in the art. The recombinant Ipf1 polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant Ipf1 is a fusion protein containing a domain which facilitates its purification, such as a glutathione-S-transferase domain or a polyhistidine leader sequence in the form of a fusion protein with the subject polypeptides.

This invention also pertains to a host cell transfected with an Ipf1 gene in order to cause expression of a recombinant form of Ipf1. The host cell may be any prokaryotic or eukaryotic cell. Thus, a nucleotide sequence derived from the cloning of the Ipf1 encoding all or a selected portion of the protein, can be used to produce a recombinant form of Ipf1 via microbial or eukaryotic cellular processes. Ligating a polynucleotide sequence into a gene construct, such as an expression vector, and transforming or transfecting host cells with the vector are standard procedures used in producing other well-known proteins, e.g. insulin, interferons, myc, p53, fos, jun, cyclins, Ikaros, and the like. Similar procedures, or modifications thereof, can be employed to prepare recombinant Ipf1, or portions thereof, by microbial means or tissue-culture technology in accord with the subject invention. Host cells suitable for expression of recombinant Ipf1 polypeptides can be selected, for example, from amongst eukaryotic (yeast, avian, insect or mammalian) or prokaryotic (bacterial) cells.

The recombinant Ipf1 gene can be produced by ligating nucleic acid encoding a Ipf1, or a portion thereof, into a vector suitable for expression in either prokaryotic cells, eukaryotic cells, or both. Expression vectors for production of recombinant forms of Ipf1 include plasmids and other vectors. For instance, suitable vectors for the expression of Ipf1 include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

Preferred mammalian expression vectors contain prokaryotic sequences to facilitate the propagation of the vector in bacteria, and one or more eukaryotic transcription regulatory sequences that cause expression of a recombinant Ipf1 gene in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found above in the description of gene therapy delivery systems.

In some instances, it may be desirable to express a recombinant Ipf1 by the use of a baculovirus expression system (see, for example, *Current Protocols in Molecular Biology*, eds. Ausubel et al. John Wiley & Sons: 1992). Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

When expression of a portion of one an Ipf1 protein is desired, i.e. a trunction mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J Bacteriol.* 169:751–XX57) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing Ipf1-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene. This type of expression system can be useful under conditions where it is desirable to produce an immunogenic fragment of an Ipf1 protein. For example, the VP6 capsid protein of rotavirus can be used as an immunologic carrier protein for portions of the Ipf1 polypeptide, either in the monomeric form or in the form of a viral particle. The nucleic acid sequences corresponding to the portion of Ipf1 to which antibodies are to be raised can be incorporated into a fusion gene construct which includes coding sequences for a late vaccinia virus structural protein to produce a set of recombinant viruses expressing fusion proteins comprising a portion of the protein Ipf1 as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of Ipf1 and the poliovirus capsid protein can be created to enhance immunogenicity of the set of polypeptide antigens (see, for example, EP Publication No: 0259149; and Evans et al. (1989) *Nature* 339:385; Huang et al. (1988) *J Virol.* 62:3855; and Schlienger et al. (1 992) J Virol. 66:2).

The Multiple Antigen Peptide system for peptide-based immunization can also be utilized to generate an immunogen, wherein a desired portion of Ipf1 is obtained directly from organo-chemical synthesis of the peptide onto an oligomeric branching lysine core (see, for example, Posnett et al. (1988) *JBC* 263:1719 and Nardelli et al. (1992) *J Immunol.* 148:914). Antigenic determinants of the subject Ipf1-binding proteins can also be expressed and presented by bacterial cells.

In addition to utilizing fusion proteins to enhance immunogenicity, it is widely appreciated that fusion proteins can also facilitate the expression and purification of proteins, such the Ipf1 polypeptides of the present invention. For example, Ipf1 can be generated as a glutathione-S-transferase (GST) fusion protein. Such GST fusion proteins can simplify purification of the recombinant protein, as for example, by affinity pruification using glutathione-derivatized matrices (see, for example, Current Protocols in Molecular Biology, eds. Ausabel et al. (N.Y.: John Wiley & Sons, 1991)). In another embodiment, a fusion gene coding for a purification leader sequence, such as a peptide leader sequence comprising a poly-(His)/enterokinase cleavage sequence, can be added to the N-terminus of the desired portion of an Ipf1 polypeptide in order to permit purification of the poly(His)-fusion protein by affinity chromatography using a $Ni^{2+}$ metal resin. The purification leader sequence can then be subsequently removed by treatment with enterokinase (e.g., see Hochuli et al. (1987) *J Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which are subsequently annealed to generate a chimeric gene sequence (see, for example, *Current Protocols in Molecular Biology*, eds. Ausubel et al. John Wiley & Sons: 1992).

The present invention also makes available isolated Ipf1 polypeptides which are isolated from, or otherwise substantially free of other cellular proteins, especially IEF1, IEF2, Isl-1 or other transcriptional regulatory factors which might be associated with Ipf1 or which bind nucleic acid containing Ipf1-responsive elements. The term "substantially free of other cellular or viral proteins" (also referred to herein as "contaminating proteins") or "substantially pure or purified preparations" are defined as encompassing preparations of Ipf1 polypeptides having less than 20% (by dry weight) contaminating protein, and preferably having less than 5% contaminating protein. Functional forms of the subject Ipf1 polypeptides can be prepared, for the first time, as purified preparations by providing recombinant proteins as described herein. By "purified", it is meant, when referring to a polypeptide or DNA or RNA sequence, that the indicated molecule is present in the substantial absence of other biological macromolecules, such as other proteins (particularly transcriptional factors, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. Moreover, in the instance of purified Ipf1, the protein preparation lacks any contaminating nucleic acids, especially nucleic acid comprising a P1 promoter sequence.

Furthermore, isolated peptidyl portions of full length forms of Ipf1 proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. Accordingly, DNA binding motifs (e.g. presumably including the homeodomain region) and activation domains which recruit other transcriptional factors (e.g. as may exist in the N-terminal fragment) can be refined to minimal sequences. For example, an Ipf1 protein may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of wild-type Ipf1 activity, such as by microinjection assays or in vitro protein or DNA binding assays. In an illustrative embodiment, peptidyl portions of Ipf1, such as derived from the amino terminal half of the protein or from the C-terminal portion, can tested for their ability to inhibit authentic Ipf1 activity by expression as thioredoxin fusion proteins, each of which contains a discrete fragment of the Ipf1 (see, for example, U.S. Pat. Nos. 5,270,181 and 5,292,646; and PCT publication WO94/02502, as well the THIOFUSION kit of Invitrogen Inc, San Diego). Such fusion proteins can be utilized in the drug screening assays described below, and, if desired, peptidyl portions which are antagnosite can be synthesized as non-peptide analogs (e.g., peptidomimetics).

It will also be possible to modify the structure of an Ipf1 polypeptide for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the Ipf1 polypeptides described in more detail herein. Such modified peptide can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the folding of the protein, and may or may not have much of an effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur -containing=cysteine and methionine (see, for example, *Biochemistry*, 2nd ed., Ed. by L. Stryer, W H Freeman and Co.: 1981). Alternatively, amino acid replacement can be based on steric criteria, e.g. isosteric replacements, without regard for polarity or charge of amino acid sidechains. Whether a change in the amino acid sequence of a polypeptide results in a functional Ipf1 homolog (e.g. functional in the sense that it acts to mimic or antagonize the wild-type form) can be readily determined by assessing the ability of the variant peptide to produce a response in cells in a fashion similar to the wild-type Ipf1 protein or competitively inhibit such a response. Peptides in which more than one replacement has taken place can readily be tested in the same manner.

This invention further contemplates a method of generating sets of combinatorial mutants of Ipf1, as well as truncation and fragmentation mutants, and is especially useful for identifying potential variant sequences (e.g. Ipf1 homologs) which are functional in Ipf1-dependent transcriptional activation, but differ from a wild-type form of the protein by, for instance, efficacy, potency and/or intracellular half-life. One purpose for screening such combinatorial libraries is, for example, to isolate novel Ipf1 homologs which function as either an agonist or an antagonist of the biological activities of the wild-type protein, or alternatively, possess novel activities all together. To illustrate, Ipf1 homologs can be engineered by the present method to provide proteins which bind to Ipf1-responsive elements yet prevent complete assembly of Ipf1-dependent transcription regulatory complexes. Such proteins, when expressed from recombinant DNA constructs, can be used in gene therapy protocols as Ipf1 antagonists.

Likewise, mutagenesis can give rise to Ipf1 homologs which have intracellular half-lives dramatically different than the corresponding wild-type protein. For example, the altered protein can be rendered either more stable or less stable to proteolytic degradation or other cellular process which result in destruction of, or otherwise inactivation of, the naturally-occurring forms of Ipf1. Such Ipf1 homologs, and the genes which encode them, can be utilized to alter the envelope of expression for a particular recombinant Ipf1 by modulating the half-life of the recombinant protein. For instance, a short half-life can give rise to more transient biological effects associated with a particular recombinant Ipf1 protein and, when part of an inducible expression system, can allow tighter control of recombinant protein levels within a cell. As above, such proteins, and particularly their recombinant nucleic acid constructs, can be used in gene therapy protocols.

In an illustrative embodiment of this method, the amino acid sequences for a population of Ipf1 homologs or other related proteins are aligned, preferably to promote the highest homology possible. Such a population of variants can include, for example, Ipf1 homologs from one or more species (e.g. orthologs), or Ipf1 homologs from the same species but which differ due to mutation, and other proteins related in some way to Ipf1. Amino acids which appear at each position of the aligned sequences are selected to create a degenerate set of combinatorial sequences. There are many ways by which the library of potential Ipf1 homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential Ipf1 sequences. The synthesis of degenerate oligonucleotides is well known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp. 273–289; Itakura et al. (1 984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87:6378–6382; as well as U.S. Pat. Nos. 5,223,409, 5,198, 346, and 5,096,815).

Alternatively, other forms of mutagenesis can be utilized to generate a combinatorial library. For example, Ipf1 homologs (both agonist and antagonist forms) can be generated and isolated from a library by screening using, for example, alanine scanning mutagenesis and the like (Rufet al. (1994) *Biochemistry* 33:1565–1572; Wang et al. (1994) *J Biol. Chem.* 269:3095–3099; Balint et al. (1993) *Gene* 137:109–118; Grodberg et al. (1993) *Eur. J Biochem.* 218:597–601; Nagashima et al. (1993) *Biol. Chem.* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11–19); or by random mutagenesis (Miller et al. (1992) *A Short Course in Bacterial Genetics*, CSHL Press, Cold Spring Harbor, N.Y.; and Greener et al. (1994) *Strategies in Mol Biol* 7:32–34).

A wide range of techniques are known in the art for screening gene products of combinatorial libraries made by point mutations, as well as for screening cDNA libraries for gene products having a certain property. Such techniques will be generally adaptable for rapid screening of the gene libraries generated by the combinatorial mutagenesis of Ipf1. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. The illustrative assays described below are amenable to high through-put analysis as necessary to screen large numbers of degenerate Ipf1 sequences created by combinatorial mutagenesis techniques.

In one screening assay, the candidate gene products are expressed in cells which are co-transfected within Ipf1-dependent reporter construct, such as the Ins-CAT vector described in Walker et al. (1983, *Nature* 306:557–561). Ipf1 homologs from the library which can mimic the function of Ipf1 (e.g. or Ipf1 agonists) will be detected by their ability to activate expression of the reporter gene. In preferred embodiments, detection and isolation of genes encoding Ipf1 agonists utilize a reporter construct which permits isolation of cells expressing these genes by providing a selectable marker such as drug resistance or luminescence. For example, a reporter construct can be provided which places the neo gene (provides resistance to G418 antibiotics) under the control of an Ipf1-responsive element, such as multiple P1 promoter sequences. Agonistic forms of Ipf1 will therefor confer resistance to G418, and permit isolation of Ipf1 clones from the library based on that selection criteria. Alternatively, the drug resistance gene can be replaced with a luminescence marker such as luciferase, such that Ipf1-induced expression is detected by luminescence of the cell. Accordingly, Ipf1 clones which activate expression of the luminescence marker can be isolated from the library by, for example, sorting the transfected cells with a fluorescence-activated cell sorter (FACS).

In similar fashion, antagonistic mutants of Ipf1 can be detected and isolated from the library based on their ability inhibit Ipf1 activation of a reporter gene. Co-transfection of cells with the constructs of the Ipf1 library, wild-type Ipf1, and a reporter gene permit this inhibitory activity to be observed. For example, the luciferase reporter described above, when transfected in a cell expressing wild-type Ipf1 and an Ipf1 mutant from the library, will be activated in cells wherein the Ipf1 mutant is an agonist, or dysfunctional (e.g. mis-folded), but repressed whenever an Ipf1 mutant antagonizes the function of the wild-type Ipf1 protein. For instance, Ipf1 homologs can be isolated from the library which the retain the ability to bind an Ipf1-responsive element, but which are defective for recruiting other transcriptional complexes to the promoter site, or alternatively, which retain the ability to bind other proteins involved in Ipf1 complexes but which are defective in binding to an Ipf1-responsive element. The reporter construct may also be generated with a marker gene whose expression is toxic or cytostatic to the host cell such that expression of an Ipf1 antagonist is detected by its ability to rescue the cell through inhibition of the reporter gene expression.

The invention also provides for reduction of the Ipf1 protein to generate mimetics, e.g. peptide or non-peptide agents, which are able to disrupt binding of Ipf1 to promoter sequences or to other regulatory proteins. Thus, such mutagenic techniques as described above are also useful to map the determinants of Ipf1 which participate in protein-protein interactions involved in, for example, forming transcriptional complexes. To illustrate, the critical residues of a Ipf1 which are involved in molecular recognition of Ipf1 can be determined and used to generate Ipf1-derived peptidomimetics that competitively inhibit binding of Ipf1 to other regulatory proteins or to Ipf1-responsive elements. By employing, for example, scanning mutagenesis to map the amino acid residues of Ipf1 apparently involved in complex formation, peptidomimetic compounds can be generated which mimic those residues, and which, by inhibiting binding of the Ipf1 to other regulatory proteins, can interfere with the function of Ipf1 in transcriptional regulation of one or more genes. For instance, non-hydrolyzable peptide analogs of such residues can be generated using retro-inverse peptides (e.g., see U.S. Pat. Nos. 5,116,947 and 5,218,089; and Pallai et al. (1983) *Int J Pept Protein Res* 21:84–92) benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1: 1231), and β-aminoalcohols (Gordon et al. (1985) *Biochem Biophys Res Commun* 126:419; and Dann et al. (1986) *Biochem Biophys Res Commun* 134:71).

Another aspect of the invention pertains to an antibody specifically reactive with an Ipf1 protein. For example, by using immunogens derived from Ipf1, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a full length Ipf1 or an antigenic fragment which is capable of eliciting an antibody response). Techniques for conferring immunogenicity on a protein or peptide include conjugation to carriers or other techniques well known in the art. An immunogenic portion of Ipf1 can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of an Ipf1 protein of the present invention, e.g. antigenic determinants of the protein represented by SEQ ID NO: 2 or a closely related human or non-human mammalian homolog thereof. For instance, a favored anti-Ipf1 antibody of the present invention does not substantially cross react (i.e. react specifically) with a protein which is less than 90 percent homologous to SEQ ID NO: 2; though antibodies which do not substantially cross react with a protein which is less than 95 percent homologous with SEQ ID NO: 2, or even less than 98–99 percent homologous with SEQ ID NO: 2, are specifically contemplated. By "not substantially cross react", it is meant that the antibody has a binding affinity for a non-homologous protein (e.g. other insulin promoter-binding proteins such as IEF2, as well as other homeobox proteins which do not bind the insulin promoter) which is at least one order of magnitude, more preferably at least two orders of magnitude and even more preferably at least 3 orders of magnitude less than the binding affinity for a protein represented by SEQ ID NO: 2.

Following immunization, anti-Ipf1 antisera can be obtained and, if desired, polyclonal anti-Ipf1 antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a Ipf1 of the present invention and monoclonal antibodies isolated from a culture comprising such hybridoma cells.

The term antibody as used herein is intended to include fragments thereof which are also specifically reactive with an Ipf1 protein. Antibodies can be fragmented using conventional techniques, including recombinant engineering, and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-Ipf1 portion.

Both monoclonal and polyclonal antibodies (Ab) directed against an Ipf1 protein can be used to block the action of that protein and allow the study of the role of Ipf1 in transcriptional regulation generally, or in the etiology of β-cell development or islet cell transformation, e.g. by microinjection of anti-Ipf1 into cells.

Antibodies which specifically bind Ipf1 epitopes can also be used in immunohistochemical staining of tissue samples in order to evaluate the abundance and pattern of expression of Ipf1. Anti-Ipf1 antibodies can be used diagnostically in immuno-precipitation and immuno-blotting to detect and evaluate Ipf1 levels in tissue or bodily fluid as part of a clinical testing procedure. For instance, such measurements can be useful in predictive valuations of the onset or progression of, for example, diabetes or other β-cell abnormalities. Likewise, the ability to monitor Ipf1 levels in the cells of an individual can permit determination of the efficacy of a given treatment regimen for an individual afflicted with such a disorder. The level of Ipf1 can be measured in cells found in bodily fluid, or can be measured in tissue, such as pancreatic biopsies. Diagnostic assays using anti-Ipf1 antibodies can include, for example, immunoassays designed to aid in early detection of β-cell necrosis (e.g. IDPM), or in the diagnosis of a neoplastic or hyperplastic disorder, and may aid in detecting the presence by detecting cells in which a lesion of the Ipf1 gene has occurred or in which the protein is misexpressed or found in abnormal protein complexes, or found in abnormally high levels in serum or plasma indicating cytolysis of β-cells.

Another application of the subject antibodies is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of μ-galactosidase amino acid sequences and whose carboxy termini consist of a foreign polypeptide. Antigenic epitopes of an lpf1 protein can then be detected with antibodies, as, for example, reacting nitrocellulose filters lifted from infected plates with anti-Ipf1 antibodies. Phage, scored by this assay, can then be isolated from the infected plate. Thus, the presence of Ipf1 homologs can be detected and cloned from other animals, including humans, and alternate isoforms (including splicing variants) can also be detected and cloned from the same species.

Moreover, the nucleotide sequence determined from the cloning of the subject Ipf1 will further allow for the generation of probes designed for use in identifying homologs in other cell types, as well as Ipf1 homologs (e.g. orthologs) from other animals. For instance, the present invention also provides a probe/primer comprising a substantially purified oligonucleotide, which oligonucleotide comprises a region of nucleotide sequence that hybridizes under stringent conditions to at least 10 consecutive nucleotides of sense or anti-sense sequence of SEQ ID NO: 1, or naturally occurring mutants thereof. In preferred embodiments, the probe/primer further comprises a label group attached thereto and able to be detected, e.g. the label group is selected from the group consisting of radioisotopes, fluorescent compounds, enzymes, and enzyme co-factors. Such probes can also be used as a part of a diagnostic test kit for identifying transformed cells, such as for measuring a level of an Ipf1 nucleic acid in a sample of cells from a patient; e.g. detecting mRNA encoding Ipf1 mRNA level or determining whether a genomic Ipf1 gene has been mutated or deleted.

In addition, nucleotide probes can be generated which allow for histological screening of intact tissue and tissue samples for the presence of an Ipf1 mRNA. Similar to the diagnostic uses of anti- Ipf1 antibodies, the use of probes directed to Ipf1 mRNAs, or to genomic Ipf1 sequences, can be used for both predictive and therapeutic evaluation of allelic mutations which might be manifest in, for example, diabetic disorders as well as neoplastic or hyperplastic disorders (e.g. unwanted cell growth) or abnormal differentiation of tissue. Used in conjunction with an antibody immunoassays, the nucleotide probes can help facilitate the determination of the molecular basis for a developmental disorder which may involve some abnormality associated with expression (or lack thereof) of Ipf1. For instance, variation in synthesis of Ipf1 can be distinguished from a mutation in the genes coding sequence.

Accordingly, the present method provides a method for determining if a subject is at risk for a disorder characterized by unwanted cell proliferation or abherent control of differentiation, particularly of pancreatic tissue. In preferred embodiments, the subject method can be generally characterized as comprising detecting, in a tissue sample of the subject (e.g. a human patient), the presence or absence of a genetic lesion characterized by at least one of (i) a mutation of a gene encoding Ipf1 or (ii) the mis-expression of an Ipf1 gene. To illustrate, such genetic lesions can be detected by ascertaining the existence of at least one of (i) a deletion of one or more nucleotides from an Ipf1 gene, (ii) an addition of one or more nucleotides to such an Ipf1 gene, (iii) a substitution of one or more nucleotides of an Ipf1 gene, (iv) a gross chromosomal rearrangement of an Ipf1 gene, (v) a gross alteration in the level of a messenger RNA transcript of an Ipf1 gene, (vi) the presence of a non-wild type splicing pattern of a messenger RNA transcript of an Ipf1 gene, and (vii) a non-wild type level of an Ipf1 protein. In one aspect of the invention there is provided a probe/primer comprising an oligonucleotide containing a region of nucleotide sequence which is capable of hybridizing to a sense or antisense sequence of SEQ ID NO: 1, or naturally occurring mutants thereof, or 5' or 3' flanking sequences or intronic sequences naturally associated with the subject Ipf1 gene. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g., U.S. Pat. Nos. 4,683,195 and 4,683,202) or, alternatively, in a ligation chain reaction (LCR) (see, e.g., Landegran et al. (1988) *Science*, 241:1077–1080; and NaKazawa et al. (1 944) *PNAS*91:360–364) the later of which can be particularly useful for detecting point mutations in an Ipf1 gene. Alternatively, immunoassays can be employed to determine the level of Ipf1 protein and/or its participation in protein complexes, particularly transcriptional regulatory complexes such as those which activate insulin expression.

Also, by inhibiting endogenous production of Ipf1, antisense techniques (e.g. microinjection of antisense molecules, or transfection with plasmids whose transcripts are anti-sense with regard to an Ipf1 mRNA or gene sequence) can be used to investigate the role of Ipf1 in growth and differentiative events, such as those giving rise to pancreatic development, as well as abnormal cellular functions in which Ipf1 may participate, e.g. in misregulation of insulin expression. Such techniques can be utilized in cell culture, but can also be used in the creation of transgenic animals.

Furthermore, by making available purified and recombinant Ipf1, the present invention facilitates the development of assays which can be used to screen for drugs which are either agonists or antagonists of the cellular function Ipf1, such as its role in the pathogenesis of proliferative and differentiative disorders, as well as in insulin regulation. For instance, an assay can be generated according to the present invention which evaluates the ability of a compound to modulate binding between Ipf1 and other transcriptional regulatory proteins or Ipf1-responsive elements. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target when contacted with a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins with a nucleic acid. Accordingly, in an exemplary screening assay of the present invention, the compound of interest is contacted with a mixture generated from an isolated and purified Ipf1 polypeptide and a nucleic acid which specifically binds Ipf1 (e.g. Ipf1-responsive element) such as the P1 insulin promoter. Detection and quantification of Ipf1/promoter complexes provides a means for determining the compound's efficacy at inhibiting (or potentiating) DNA binding by Ipf1. Similarly, other regulatory proteins which are identified as binding Ipf1 can be used in place of the nucleic acid. The efficacy of the compound can be assessed by generating dose response curves from data obtained using various concentrations of the test compound. Moreover, a control assay can also be performed to provide a baseline for comparison. In the control assay, isolated and purified Ipf1 is added to a composition containing the nucleic acid (or the other regulatory proteins), and the formation of Ipf1-containing complexes is quantitated in the absence of the test compound.

The formation of complexes including Ipf1 may be detected by a variety of techniques. For instance, modulation in the formation of complexes can be quantitated using, for example, detectably labelled proteins (e.g. radiolabelled, fluorescently labelled, or enzymatically labelled), by immunoassay, or by chromatographic detection.

Typically, it will be desirable to immobilize either the Ipf1 protein or the DNA or other regulatory protein (hereinafter "target molecule") to facilitate separation of target/Ipf1 complexes from uncomplexed forms, as well as to accomadate automation of the assay. In an illustrative embodiment, a fusion protein can be provided which adds a domain that permits Ipf1 to be bound to an insoluble matrix. For example, glutathione-S-transferase/Ipf1 (GST/Ipf1) fusion proteins can be adsorbed onto glutathione sepharose beads (Sigma Chemical, St. Louis, Mo.) or glutathione derivatized microtitre plates, which are then combined with the target molecule, e.g. an $^{35}$S-labeled protein or DNA fragment, and the test compound, and mixture incubated under conditions conducive to complex formation. Following incubation, the beads are washed to remove any unbound target molecule and the matrix bead-bound radiolabel determined directly (e.g. beads placed in scintilant), or in the superntantant after the complexes are dissociated, e.g. when microtitre plates are used. Alternatively, after washing away unbound protein, the complexes can be dissociated from the matrix, separated by SDS-PAGE gel, and the amount of target molecules found in the matrix-bound fraction quantitated from the gel using standard electrophoretic techniques.

Other techniques for immobilizing proteins or DNA on matrices are also available for use in the subject assay. For instance, the DNA target protein can be immobilized utilizing conjugation of biotin and streptavidin. Biotinylated DNA can be prepared using techniques well known in the art and immobilized in the wells of streptavidin-coated 96 well plates (Pierce Chemical) and Ipf1 binding to the immobilized nucleic acid detected. Exemplary methods for detecting such complexes, in addition to those described above for the GST-immobilized Ipf1 complexes, include immunodetection of complexes using antibodies reactive with Ipf1 as well as enzyme-linked assays which rely on detecting an enzymatic activity associated with Ipf1. In the instance of the latter, the enzyme can be chemically conjugated or provided as a fusion protein with the Ipf1 polypeptide. To illustrate, Ipf1 can be chemically cross-linked with alkaline phosphatase, and the amount of Ipf1 trapped in the complex can be assessed with a chromogenic substrate of the enzyme, e.g. paranitrophenyl phosphate. Likewise, a fusion protein comprising the Ipf1 and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quatitating Ipf1 trapped in the complex, antibodies against the protein, such as the anti-Ipf1 antibodies described herein, can be used. Alternatively, the protein to be detected in the complex can be "epitope tagged" in the form of a fusion protein which includes, in addition to Ipf1 sequences, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

In another embodiment, the assay format is derived in a similar manner to the use of Ipf1-sensitve reporter constructs described above. For example, co-transfection of an Ipf1-deficient cell (e.g. a COS or CHO cell) with an Ipf1 expression vector and an Ipf1-dependent reporter construct provides a convenient system for identifying compounds based on their ability to affect Ipf1-dependent transcription.

Additionally, Ipf1 can be used to generate an interaction trap assay (see, U.S. Pat. No. 5,283,317; PCT publication WO94/10300; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696), for detecting agents which either potentiate or attenuate complex formation between a Ipf1 and other transcriptional regulatory proteins. Indeed, an interaction trap assay generated with Ipf1 as a bait protein can be used to identify other cellular proteins which bind Ipf1, and which would therefore be implicated in Ipf1 transcriptional regulation, such as by participating in regulatory complexes, or by causing post-translational modification (e.g. phosphenylation or ubiquitination) of Ipf1.

The interaction trap assay relies on reconstituting in vivo a functional transcriptional activator protein from two separate fusion proteins, one of which comprises the DNA-binding domain of a transcriptional activator fused to an Ipf1 polypeptide (which preferably lacks its own DNA binding ability). The second fusion protein comprises a transcriptional activation domain (e.g. able to initiate RNA polymerase transcription) fused to a protein which binds Ipf1. When the two fusion proteins interact, the two domains of the transcriptional activator protein are brought into sufficient proximity as to cause transcription of a reporter gene. In an illustrative embodiment, *Saccharomyces cerevisiae* YPB2 cells are transformed simultaneously with a plasmid encoding a GAL4db-Ipf1 (Δ homeodomain) fusion (db: DNA binding domain) and with a plasmid encoding the GAL4 activation domain (GAL4ad) fused to an Ipf1-binding protein, wherein Ipf1 (Δ homeodomain) designates an Ipf1 mutant lacking a homeodomain able to an Ipf1-responsive ement, such as an Ipf1 in which His-190 is deleted, or wherein the protein is truncated (e.g. comprises residues 1–145). Moreover, the strain is transformed such that the GAL4-responsive promoter drives expression of a phenotypic marker. For example, the ability to grow in the absence of histidine can depends on the expression of the HIS3 gene. When the HIS3 gene is placed under the control of a GAL4-responsive promoter, relief of this auxotrophic phenotype indicates that a functional GAL4 activator has been reconstituted through the interaction of the target protein and Ipf1. Thus, agents able to inhibit Ipf1 interaction with target protein will result in yeast cells unable to growth in the absence of histidine. Alternatively, the phenotypic marker (e.g. instead of the HIS3 gene) can be one which provides a negative selection when expressed such that agents which disrupt this Ipf1-dependent interaction confer positive growth selection to the cells. Comercial kits which can be modified to develop two-hybrid assays with the subject Ipf1 are presently available (e.g., MATCHMAKER kit, ClonTech catalog number K 1605-1, Palo Alto, Calif.). This assay can also be used to screen cDNA libraries for Ipf1 interactors, by generating a library of cDNA:Ad constructs.

Another aspect of the present invention concerns transgenic animals which are comprised of cells (of that animal) which contain a transgene of the present invention and which preferably (though optionally) express an exogenous Ipf1 in one or more cells in the animal. The Ipf1 transgene can encode the wild-type form of the protein, or can encode homologs thereof, including both agonists and antagonists, as well as antisense constructs designed to inhibit expression of the endogenous gene. In preferred embodiments, the expression of the transgene is restricted to specific subsets of cells, tissues or developmental stages utilizing, for example, cis-acting sequences that control expression in the desired pattern. In the present invention, such mosiac expression of the subject Ipf1 can be essential for many forms of lineage analysis and can additionally provide a means to assess the effects of, for example, antagonism of Ipf1 action, which deficiency might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of Ipf1 or in disruption of the coding sequence. For example, excision of a target sequence which interferes with the expression of a recombinent Ipf1 gene can be designed to activate expression of that gene. This interference with expression of the protein can result from a variety of mechanisms, such as spatial separation of the gene from a promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation. Alternatively, recombinase sites can be placed in intronic sequence and, by homologous recombination inserted into the genomic Ipf1 gene such that inversion of excisim of the target sequence inactivates the Ipf1 allele.

In an illustrative embodiment, either the crelloxP recombinase system of bacteriophage P1 (Lakso et al. (1 992) *PNAS* 89:6232–6236; Orban et al. (1992) *PNAS* 89:6861–6865) or the FLP recombinase system of *Saccharomy cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation or exogenous expression of a Ipf1, or alternatively, disruption of the endogenous Ipf1 gene, can be regulated via regulation of recombinase expression.

Use of the cre/loxP recombinase system to regulate expression of a recombinant Ipf1 gene, requires the construction of a transgenic animal containing transgenes encoding both the Cre recombinase and the subject protein. Animals containing both the Cre recombinase and the recombinant Ipf1 gene can be provided through the construction of "double" transgenic animals. A convenient method for providing such animals is to mate two transgenic animals each containing a transgene, e.g., the Ipf1 gene in one animal and recombinase gene in the other. Similar transgene manipulation can be used to generate animals dependent on recombinase expression for disruption of the Ipf1 gene.

One advantage derived from initially constructing transgenic animals containing a transgene in a recombinase-mediated expressible format derives from the likelihood that the subject protein will be deleterious upon expression in the transgenic animal such as the pancreas deficient mice described below. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic Ipf1 transgene is silent will allow the study of progeney from that founder in which disruption of Ipf1 transcriptional regulatory complexes in a particular tissue or at certain developmental stages would result in, for example, a lethal phenotype.

Similar conditional transgenes can be provided using either prokaryotic or viral promoter sequences which require prokaryotic or viral proteins to be simultaneous expressed in the cell in order to facilitate expression of the transgene. Exemplary promoters and the corresponding trans-activating prokaryotic proteins are given in U.S. Pat. No. 4,833,080, and conditional viral expression systems are provided in U.S. Pat. No. 5,221,778. Moreover, expression of the conditional transgenes can be induced by gene therapy-like methods wherein a gene encoding the trans-activating protein, e.g. a recombinase or a prokaryotic protein, is delivered to the tissue and caused to be expressed using, for example, one of the gene therapy constructs described above. By this method, the Ipf1 transgene could remain silent into adulthood and its expression "turned on" by the introduction of the trans-activator.

Methods of making transgenic animals are well known in the art. For example, see *Manipulating the Mouse Embryo*, (Cold Spring Harbor Laboratory Press, Cold Spring Harbor, N.Y., 1986), and U.S. Pat. Nos. 5,347,075; 5,322,775; 5,221,778; 5,175,385; 5,175,384; 5,175,383; 5,087,571; and 4,736,866.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

For construction of transgenic mice, procedures for embryo manipulation and microinjection are described in Hogan et al. *Manipulating the Mouse Embryo*, (Cold Spring Harbor Laboratory Press, Cold Spring Harbor, N.Y., 1986).

Similar methods are used for production of other transgenic animals. In an exemplary embodiment, mouse zygotes are collected from six week old females that have been superovulated with pregnant mares serum (PMS) followed 48 hours later with human chorionic gonadotropin. Primed females are placed with males and checked for vaginal plugs on the following morning. Pseudopregnant females are selected for estrus, placed with proven sterile vasectomized males and used as recipients. Zygotes are collected and cumulus cells removed by treatment with hyaluronidase (1 mg/ml). Pronuclear embryos are recovered from female mice mated to males. Females are treated with pregnant mare serum, PMS, (5 IU) to induce follicular growth and human chorionic gonadotropin, hCG (51 U) to induce ovulation. Embryos are recovered in a Dulbecco's modified phosphate buffered saline (DPBS) and maintained in Dulbecco's modified essential medium (DMEM) supplemented with 10% fetal bovine serum.

Microinjections can be performed, for example, using Narishige micromanipulators attached to a Nikon diaphot microscope. Embryos are held in 100 microliter drops of DPBS under oil while being microinjected. DNA solution is microinjected into the largest visible male pronucleus. Successful injection is monitored by swelling of the pronucleus. Immediately after injection embryos are transferred to recipient females, mature mice mated to vasectomized male mice. Recipient females are anesthetized using 2,2,2-tribromoethanol. Paralumbar incisions are made to expose the oviducts and the embryos are transformed into the ampullary region of the oviducts. The body wall is sutured and the skin closed with wound clips. Recipients are appropriately ear notched for identification and maintained until parturition.

To identify transgenic offspring, particularly where conditional transgenic systems have been employed such that no phenotypic trait is apparent absent induction, standard tail samples can be used to assess incorporation of the transgene. For example, at three weeks of age, about 2–3 cm long tail samples are excised for DNA analysis. The tail samples are digested by incubating overnight at 55° C. in the presence of 0.7 ml 50 mM Tris, pH 8.0, 100 mM EDTA, 0.5% SDS and 350 $\mu$g of proteinase K. The digested material is extracted once with equal volume of phenol and once with equal volume of phenol:chloroform (1:1 mixture). The supernatants are mixed with 70 $\mu$l 3 M sodium acetate (pH 6.0) and the DNAs are precipitated by adding equal volume of 100% ethanol. The DNAs are spun down in a microfuge, washed once with 70% ethanol, dried and dissolved in 100 $\mu$l TE buffer (10 mM Tris, pH 8.0 and 1 mM EDTA). 10 to 20 $\mu$l of DNAs were cut with restrictions based on the transgene map, electrophoresed on agarose gels, blotted onto nitrocellulose paper and hybridized with $^{13}$P-labeled probes described herein.

Retroviral infection can also be used to introduce a Ipf1 transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–693 1; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making knock-out or disruption transgenic animals are also generally known. See, for example, *Manipulating the Mouse Embryo,* (Cold Spring Harbor Laboratory Press, Cold Spring Harbor, N.Y., 1986). An exemplary knock-out mouse is described in the examples below. As set out above, recombinase-dependent knockouts can also be generated, e.g. by homologous recombination to insert recombinase target sequences, such that tissue specific and/or temporal control of inactivation of the endogenous Ipf1 gene can be controlled as above.

EXEMPLIFICATION

The invention now being generally described, it will be more readily understood by reference to the following examples which are included merely for purposes of illustration of certain aspects and embodiments of the present invention, and are not intended to limit the invention.

Example 1

Cloning and Expression of Ipf1

As described below, a cDNA encoding Ipf1, a novel mammalian homeodomain-containing protein, has been isolated. Ipf1 is apparently expressed predominantly in the β-cells of normal adult mouse pancreas, and it binds to and transactivates the insulin promoter, providing evidence that Ipf1 is directly involved in the selective β-cell expression of the insulin gene. In mouse embryos, Ipf1 expression is initiated prior to hormone gene expression and restricted to the ventral and dorsal walls of primative foregut at positions where pancreas will later form. The pattern of Ipf1 expression and its ability to stimulate insulin gene transcription suggests that Ipf1 functions both in the early specification of the primative gut to a pancreatic fate and in the maturation of the pancreatic β-cell.

The transcriptional activity of the rat insulin I 5' flanking DNA is to a large extent mediated by the enhancer element which contains binding sites for a number of trans-acting nuclear proteins that each contribute to the overall activity of the enhancer (German et al., (1992) *Genes Dev* 6:2165–2176). Although the enhancer element is dominant, it has previously been shown that the proximal 'promoter' sequences have a low intrinsic cell specific activity (Edlund et al., (1985) *Science* 231:912–916). As described herein, mutation of the P1 promoter site results in a 2.5-fold decrease in transcriptional activity of the whole insulin 5' flank. It is also demonstrated that recombinant Ipf1 binds to the P1 site and is capable of increasing the activity of the complete insulin 5' flanking DNA in transiently transfected insulin-producing βTC1 cells and that this transactivation is dependent on the P1 promoter site. Ipf1 can also transactivate multimers of the P1 site linked to a heterologous TATA box in non-βcells. The relatively low degree of transactivation by Ipf1 of the isolated P1 site probably reflects the need for multiple transacting factors in the transcriptional regulation of the insulin gene. Since Ipf1 is restricted to the β-cells of adult pancreas and binds to and transactivates the insulin promoter, it is very likely that Ipf1 in vivo contributes to the β-cell specific activity of the insulin promoter. Ipf1 may also contribute to other aspects of the β-cell phenotype.

In the mouse, morphogenesis of the pancreas begins by evagination of the duodenum at the 26 somite stage (e9.5) (Gittes (1992) *PNAS* 89:1128–1132, but the midgut and adjacent tissue of mouse embryos acquire the ability to form exocrine pancreas tissue in vitro at about the 8 somite stage. By the 10 somite stage, a region of the gut itself can be identified as the precursor of exocrine pancreas (Wessells et al. (1967) *Dev. Biol.* 15:237–270). The onset of Ipf1 protein expression at around the 13 somite stage supports a role for Ipf1 in the commitment of the primitive foregut endoderm to a pancreatic fate. At this early stage of development, no "pancreatic" mesoderm or even loose mesoderm is associated with the dorsal gut endoderm which instead is in close proximity to the notochord (Wessells et al. supra). The notochord is known as a source of inductive signals that contribute to the regionalization of the neural plate (Yamada et al., (1991) *Cell* 64:635–647); Ericson et al., (1992) *Science* 256:1555–1560). A putative role of the notochord in the early inductive events leading to the regionalization of the gut endoderm can now be studied using Ipf1 as a marker.

Since the onset of Ipf1 expression (e8.5) is correlated with the commitment of the gut endoderm to a pancreatic fate, this early pattern of Ipf1 expression may reflect the specification of pluripotent pancreatic stem cells that are the progenitors of all the various pancreatic cells. However, it has recently been shown that hormone gene transcripts are present at 20 somites, prior to morphogenesis, and that exocrine gene expression is initiated well after the formation of the pancreatic diverticulum (Gittes et al., supra). These results, which indicate that the endocrine cells are specified before the exocrine ones, may suggest that the early Ipf1-expressing cells are the progenitors only of the β-cells rather than of all pancreatic cells.

While it is not clear that there exists a precise lineage relationship between the different pancreatic hormone-producing cells, a number of independent studies of normal embryonic islet cells and of different islet tumor cell lines have shown that certain hormones can be co-expressed in the same cells (Yoshinari et al. (1992) *Anat Embryol* 105:63–70; Madsen et al., (1986) *J Cell Biol* 103:2025–2034; Teitelman et al., (1987) *Dev Biol* 121:454–466; Alpert et al., (1988) *Cell* 53:295–308: Herrera et al., (1991) *Development* 113:1257. These studies have also suggested that the terminal differentiation of individual islet cell types occurs late in development. There is not complete agreement on which of the hormones can be colocalized, but taken together the results favor the hypothesis of a common pancreatic endocrine cell lineage (Alpert et al., supra; Herrera et al., supra; Gittes et al. supra). It has been suggested that at e15.5, about half of the insulin-producing cells also express glucagon but a different study claims that in the mouse there is never any co-expression of these two hormones. Since, as described below, Ipf1 becomes restricted to the insulin-producing cells very early in development and since no apparent co-expression of Ipf1 and glucagon is observed, these results also suggest that the (α- and β-cells develop independently.

It is noted that expression of XlHbox8 is also restricted to epithelial cells of the duodenum and the developing pancreas, but in adults XlHbox8 is only found in the nuclei of the pancreatic excretory ducts: no expression is evident in the pancreatic islet cells (Wright et al., (1988) *Development* 104:787–794. The differences in amino acid sequence and in the pattern of expression of these proteins suggest that either Ipf1 is a mouse homolog of XlHbox8 which has diverged both with respect to structure and function, or that there exist at least two related homeodomain proteins which are both involved in pancreas development. By using affinity purified antibodies, the experiments described below have avoided cross-reaction with a putative XlHbox8 mouse homolog. Moreover, IPF1 genomic DNA has been isolated and characterized, but by using the IPF1 homeobox probe in low stringency hybridization these experiments so far failed to detect any Ipf1-related gene. Similarly, the Xenopus DNA fragment encoding the C-terminal part of the XlHbox8 gene has been isolated but no cross-hybridization has been detected with the mouse genomic DNA fragment. However, since these results are negative, the possibility that the mouse genome contains a true XlHbox8 homolog cannot be excluded, and likewise, neither can alternative splicing be excluded as a way of generating different polypeptides having an identical homeodomain.

Other homeodomain proteins, like members of the POU, LIM and Nkx-2 families, are expressed at high levels in subsets of adult cell types and are implicated in transcriptional control in terminally differentiated cells (Herr et al.,(1988) *Genes Dev* 2:1515–1516; Freyd et al., (1990) *Nature* 344:875–878; Karlsson et al., (1990) *Nature* 344:879–882; Price et al., (1992) *Neuron* 8:241–255). In some aspects, Ipf1 resembles the POU Pit-1/GHF-1 protein in that both proteins are selectively expressed in polypeptide hormone-producing cells and transcriptionally regulate specific hormone genes (Bodner et al., (1988) *Cell* 55:505–518; Ingraham et al., (1988) *Cell* 55:519–529). Mutations of the Pit-1/GHF-1 gene in dwarf mice result in hypoplasia of the Pit-expressing cells, providing evidence for a role of Pit-1 in specification of these cell types (Li et al., (1990) *Nature* 347:528–533). It is proposed that Ipf1 may have a similar function in the development of the pancreas.

Moreover, temporal expression pattern of IPF1 resembles that of the lymphoid-specific transcriptional factor Ikaros, the RNA for which is highly expressed in the early fetal liver and which then starts to decline at e14 (Georgopoulos et al., (1992) *Science* 258:808–812). It has been argued that the early high level expression of Ikaros is necessary for further commitment and differentiation of the pluripotent hematopoietic stem cell, and it has been suggested that the decrease in expression represents changes in the developmental profile of hematopoietic progenitors towards a more committed erythroid stage (Georgopoulos et al., supra). Ipf1 may have a similar dual function in the development of the pancreas and the β-cells.

i) Cloning of cDNAs Encoding IPF1

The islet-cell specific expression of the rat insulin I gene is dependent both on a distal enhancer element and on more proximal "promoter" sequences which do not contribute to the enhancing activity. The rat insulin I gene, for example, contains a short DNA element, TAATGGG, which is located at positions −80 to −74 and which is conserved in the rat, mouse, guinea pig and human insulin promoters (Steiner et al., (1985) *Anna Rev Genet*).

To isolate the gene encoding the putative transcriptional regulatory protein which binds this site, a set of degenerate PCR primers were designed that were complementary to a consensus sequence of helix 3 of known homeodomain proteins (see Materials and methods). Lacking any information on the possible structure of IPF1, a primer complementary to sequences in the λgt11 vector was used as the second primer in the PCR. These two sets of primers were used in PCR on total phage DNA prepared from a phage stock of a βTC1 λgt11 cDNA library. By cloning and sequencing the DNA fragments obtained in the PCR, a 100 bp fragment was identified which showed an open reading frame encoding a partial homeodomain. Using this fragment as a probe, overlapping cDNAs encoding a protein of 284 amino acids with a calculated molecular weight of 31 kDa were isolated from the same library.

Figure 1B:
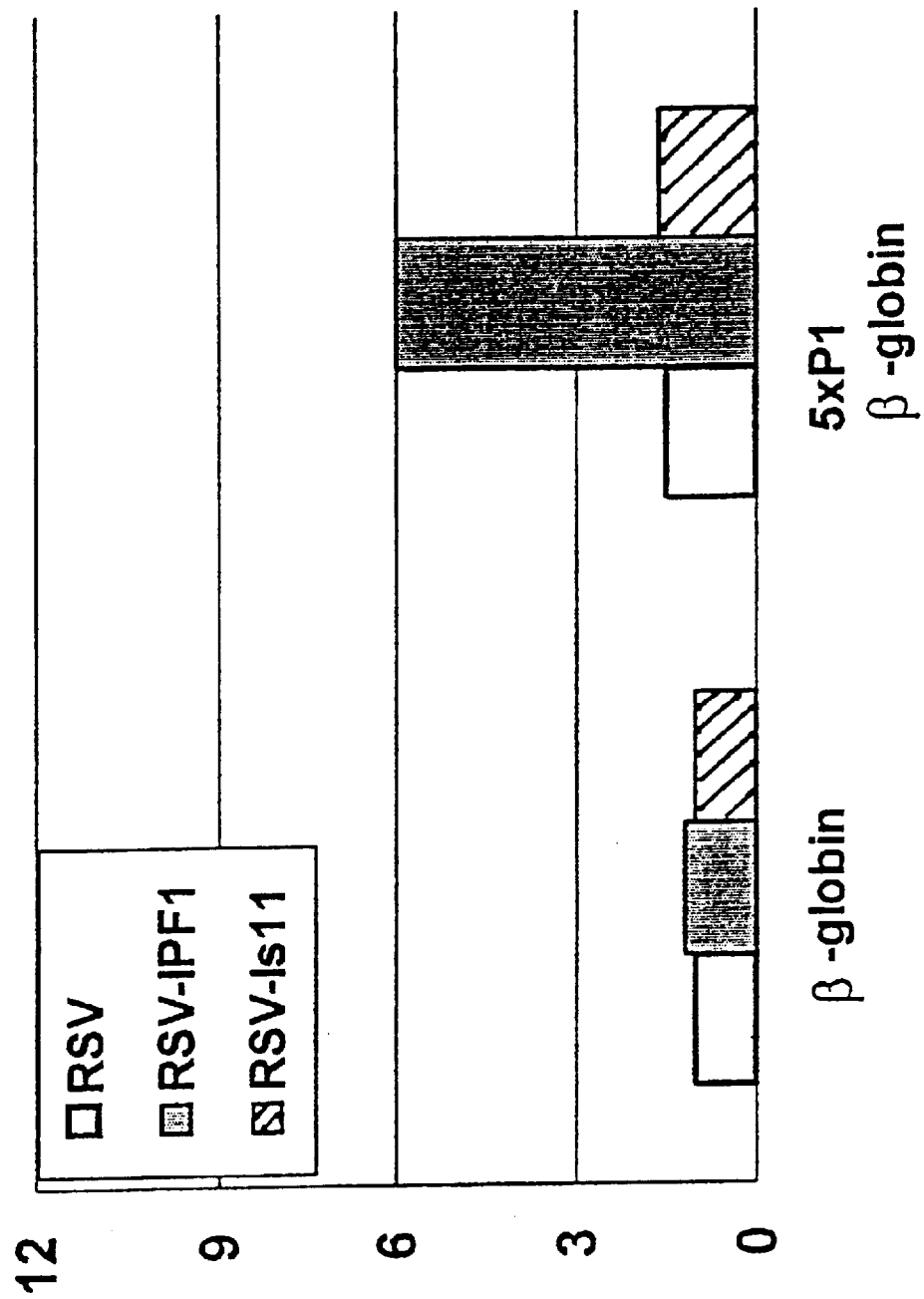

The encoded protein IPF1 was so named for reasons presented below. The deduced amino acid sequence revealed a homeodomain which is divergent from the Antennapedia prototype and which contained a unique histidine in position 45 of helix 3 (His-190, SEQ ID NO. 2). This homeodomain is not identical to any previously isolated mammalian homeodomain protein, but part of the homeodomain is identical to the known part of the homeodomain of the XlHbox8 protein from *Xenopus laevis* (Wright et al., (1988) 104:787–794) (FIG. 1B). Only the C-terminal part, including roughly two-thirds of the homeodomain, of XLHbox8 has been reported. No homology outside of the homeodomain is observed between these two proteins. A genomic DNA fragment has been isolated from the leech *Helobdella triseralis*, which encodes a homeodomain sharing some homology with the IPF1 and XlHbox8 proteins (Weeden et al., (1 990) *Nu. Acid Res* 18:1908). Only the sequence of the homeodomain of this protein, Htr-A2, has been published but it is 86% homologous to the IPF1 homeodomain and has the characteristic histidine in helix 3. No additional information is available regarding this protein.

RNA prepared from the IPF1 cDNA template was translated in vitro and the DNA binding specificity of the in vitro translation product was determined using an electrophoretic mobility shift assay (EMSA) and the insulin promoter P1 site as a probe (Ohisson et al., (1991) *Mol Endocrin* 5:897–904; see also Materials and Methods below). The in vitro translation product bound to the P1 element and migrated to the same relative position in the gel as IPF1 from the βTC1 nuclear extract. Competition studies with wild-type and mutant P1 sites showed that the in vitro translation product had the same binding specificity as the endogenous IPF1.

As described below, antibodies were raised against the C-terminal half of the encoded protein, carrying 48 amino acids of the homeodomain. The obtained antiserum was shown to block binding of nuclear Ipf1 to the P1 site, but did not recognize other homeodomain proteins like Isl-1 (Karlsson et al., (1990) *Nature* 344:879–882). To show that the cloned cDNA encoded IPF1, antibodies directed against the part of Ipf1 located C-terminally to the homeodomain were affinity purified using the glutathione S-transferase (GST) gene fusion system (see Materials and methods). These affinity purified antibodies, which recognize the C-terminal part but not the homeodomain of IPF1, gave rise to a supershifted complex of nuclear IPF1 bound to the P1 site. Collectively, these results indicate that the isolated cDNA encodes IPF1.

ii) Ipf1 Transactivates the Insulin Promoter

Figure 1C:
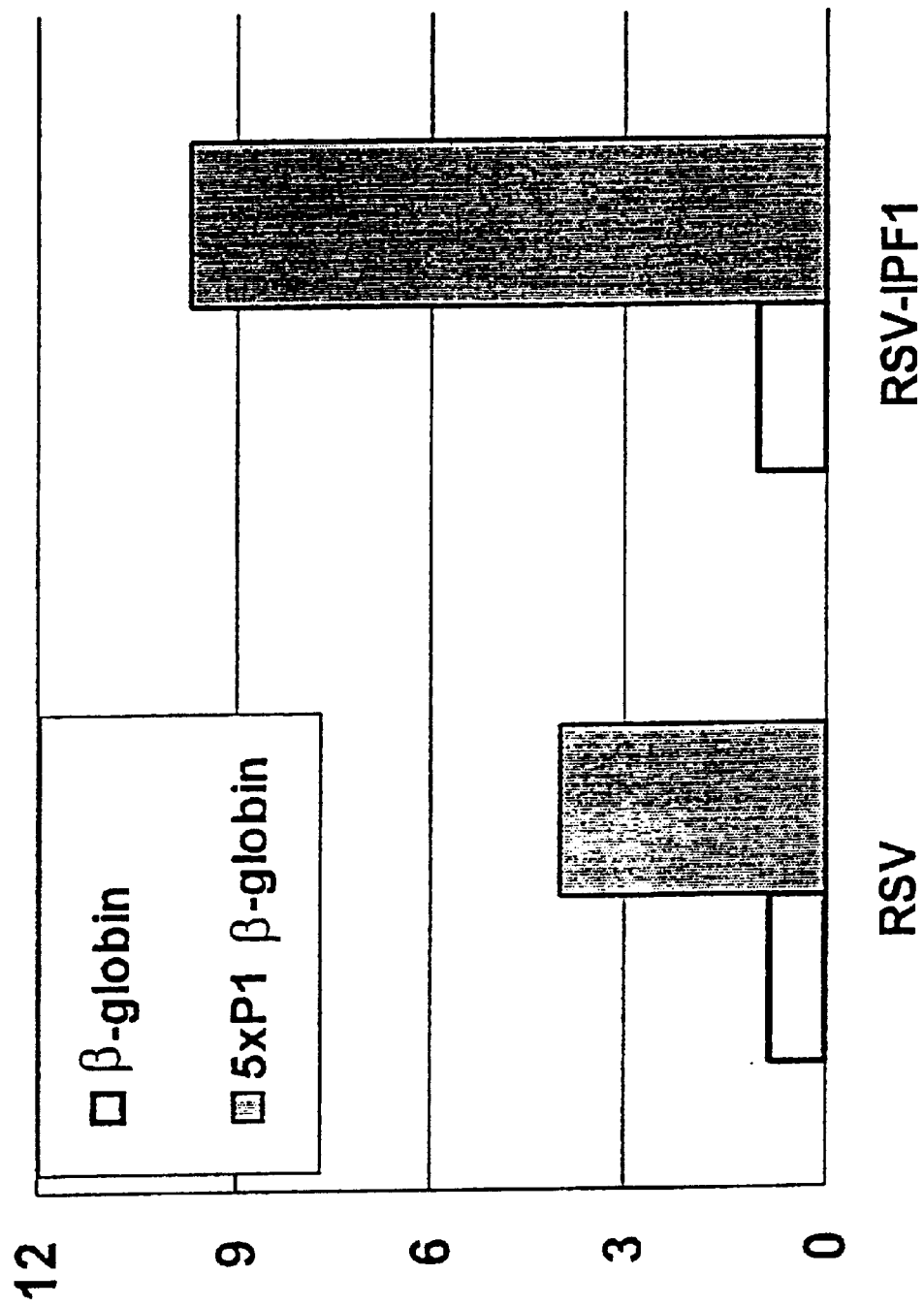

Sequences immediately upstream of the insulin gene TATA box, which include the P1 promoter site, have previously been shown to be of importance for the transcriptional activity of the insulin 5' flanking DNA and to be preferentially active in pancreatic endocrine cell lines (Edlund et al., (1985) *Science* 230:912–916. It is demonstrated herein that a 5' flank where the AA residues in the TAATGGG IPF1 binding site have been changed to CC, and to which IPF1 fails to bind, has a 2.5-fold lower activity than the wild-type 5' flank in βTC1 cells (FIG. 1A). This result is in contrast to previously published results (Karlsson et al., (1987) *PNAS* 84:8819–8823). The activity of the wild-type insulin 5' flank in βTC1 cells was further increased by co-transfection with a vector in which Ipf1 expression is under the control of the Rous sarcoma virus (RSV) long terminal repeat (FIG. 1A) and, as expected, the mutant 5' flank could not be transactivated by Ipf1. Ipf1 was also tested to see if it could transactivate a construct carrying five copies of the P1 site linked to the β-globin TATA box in non-pancreatic cells. If Ipf1 could transactivate this construct, it should be preferentially active in Ipf1-containing insulin-producing cells. Therefore, the intrinsic cell specificity of this construct was analyzed and found that it was, relative to the control TATA box construct, 3-fold more active in the βTC1 cells than in the CHO cells (FIGS. 1B and 1C). By expressing Ipf1 in the CHO cells, the activity of the 5×P1 construct was increased to that seen in the βTC1 cells (FIG. 1B). The activity of the 5×P1 construct could also be increased 2-fold in the βTC1 cells by co-transfection with the RSV-Ipf1 expression vector (FIG. 1C). As a specificity control, an RSV-Isl-1 expression construct was shown to not be able to transactivate the 5×P1 β-globin construct in the CHO cells (FIG. 1B ).

iii) Ipf1 is Selectively Expressed in the Adult Pancreatic β-Cells

Native Ipf1 is detected in nuclear extracts prepared from insulin-producing βTC1 cells but not in nuclear extracts prepared from glucagon-producing αTC1 cells or from non-endocrine cells. Utilizing Northern analysis of RNA prepared from αTC1 cells, βTC1 cells, and a variety of other mouse cell lines and organs, a 2.3 kb IPF1 transcript was detected only in βTC1 cells. Ipf1 RNA was also found to be present in insulin-producing cell lines from other species. As a test of the differentiated state of the αTC1 and βTC1 cells used, RNA from these cells was probed with insulin and glucagon cDNA.IT was observed that very little or no co-expression of these genes occurs.

The pattern of expression of IPF1 in adult mouse pancreas was analyzed at the single cell level by immunohistochemistry using affinity purified anti-Ipf1 antibodies (see Materials and methods). Immunoreactivity was readily detectable within the islets whereas no staining was observed in the exocrine pancreas or within the duct cells. Within the islets, the staining paralleled the typical pattern for insulin-producing cells since the majority of the cells were positive and were all located in the center of the islets and double immunostaining using anti-IPF1 and anti-hormone antibodies showed that Ipf1 was not present in glucagonand somatostatin-producing cells. Since IPF1 is apparently restricted to the β-cells of adult pancreas and since it binds to and transactivates the insulin promoter, it is very likely that IPF1 is directly involved in the control of the β-cell specific activity of the insulin gene.

iv) Ipf1 is Selectively Expressed in the Pancreatic Progenitor Cells in Early Mouse Embryos The affinity purified anti-Ipf1 antibodies were employed for immunohistochemistry on cryostat sections of mouse e8.5–15.5 embryos to study the temporal and spatial pattern of IPF1 expression at the single cell level. At all stages of development, Ipf1 expression was only detected in the pancreatic anlagen or in the pancreas itself. In both sagittal and transverse sections of 18–20 somite embryos, IPF1 positive cells are present in the part of duodenum which will later give rise to the dorsal and ventral pancreas. By using whole-mount immunohistochemistry (see Materials and methods) it was conclusively demonstrated that Ipf1 is only expressed in the dorsal and ventral walls of the duodenum and not in the lateral parts of the gut wall. Thus, Ipf1 expression is restricted to the sites where the dorsal and ventral pancreas will start to evaginate. At the 18–20 somite stage the majority of the cells in these two regions are IPF1 positive. Moreover, a few IPF1 positive cells can be detected as early as the 13 somite stage (e8.5) in both the dorsal and ventral walls of the duodenum, whereas no Ipf1 positive cells were detected at the 10 somite stage.

In the mouse pancreas a few insulin-containing cells appear around e12 in the dorsal bud and a day or so later in the ventral bud. Glucagon-containing cells are already present at e10.5 in the dorsal bud (Herrera et al., (1991) *Development* 113:1257–1265). Using anti-hormone antisera and affinity purified anti-Ipf1 antibodies, the pattern of expression of Ipf1 was correlated with that of glucagon and insulin. It was observed that there was a drastic decrease in the relative number of Ipf1-expressing cells between e10.5 and e11.5. At e13.5 there were still very few Ipf1 expressing cells and none or very few of the glucagon-expressing cells express Ipf1. This relative decrease in the number of Ipf1 positive cells is most likely the result of ingrowth of the exocrine parenchyma which would result in the dispersion of the Ipf1 positive cells. At e15.5, the relative number of Ipf1 positive cells has increased substantially and at this stage the pancreas contains both insulin- and glucagon-producing cells but apparently only the insulin-producing cells express Ipf1. The increase in the relative number of Ipf1-expressing cells between e13.5 and e15.5 correlates with a previous observation of a 20-fold relative increase in the number of insulin-producing β-cells during this period (Herrera et al., supra).

v) Materials and Methods

Polymerase Chain Reaction and Isolation of cDNA Clones

The following combinations of oligonucleotides were used in the PCRs: a set of degenerate oligonucleotides complementary to a consensus sequence of helix III of known homeoboxes, (SEQ ID NO: 3) 5'-GCAAGCTTCATIC$^T/_G$IC$^T/_G$$^G/_A$TT$^C/_T$TG$^G/_A$AACCA-3', was combined with either of the two oligonucleotides included in the λgt11 insert screening amplimer set (cat. no 5412-1, Clontech Laboratories Inc., Palo Alto, Calif.). The DNA template was prepared from a βTC1 λgt11 library (Walker et al., (1990) *Nuc. Acid Res.* 18:1109–1176. An aliquot of this library was dialyzed against distilled water and then frozen, thawed and used in the PCRs which were carried out using Taq DNA polymerase (Perkin-Elmer/Cetus) according to the manufacturer's instructions. The PCR product of interest was sequenced and subsequently labelled with [α-$^{32}$P]dATP and used as a probe to screen the βTC)λgt11 in order to isolate a full-length cDNA clone.

Nuclear Extract Preparation and DNA Transfections

Nuclear extract was prepared from βTC1 cells, a transgenically derived insulin-producing β-cell line (Efrat et al., (1988) *PNAS* 85:9037–9041), as previously described (Ohisson and Edlund, (1986) *Cell* 45:35–44). DNA transfections of βTC1 and CHO cells were carried out as described previously (Walker et al., (1983) *Nature* 306:557–581).

In vitro Transcription and Translation

The Isl-1 template for SP6 polymerase-directed in vitro transcription has been described earlier (Ohisson et al., (1991) *Mol Endocrinol* 5:897–904). The IPF1 template was constructed by inserting the full-length Ipf1 cDNA into the vector pGEM 3. The template was linearized before T7 polymerase-directed in vitro transcription. In vitro translation in rabbit reticulocyte lysates was carried out as recommended by the manufacturer (Promega, Madison, Wis.).

Electrophoretic Mobility Shift Assay

The following oligonucleotides were used in the EMSA: wild-type promoter element P1: (SEQ ID NO: 4) GCCCT-TAATGGGCCAAACGGCA; P1 mutant 1: (SEQ ID NO: 5) GGGGTTAATGGGCCAAACGGCA; P1 mutant 2: (SEQ ID NO: 6) GCCCTTCCTGGGCCAAACGGCA; P1 mutant 3: (SEQ ID NO: 7) GCCCTTAATCCCCCAAACGGCA; and wild-type enhancer element E2: (SEQ ID NO: 8) GCCCCTTGTTAATAATCTAAT (Ohisson et al., (1991), supra). These oligonucleotides were all custom-made by Symbicom AB (Umea, Sweden). The oligonucleotides were annealed, end-labelled and purified as previously described (Ohlsson et al., (1988), supra). The EMSA was carried out as described previously (Ohlsson et al., (1988), supra). The antisera used were added together with nonspecific DNA {poly[d(I-C)]:poly[d(A-T)], 1:1 ratio} 15–20 min before the specific end labelled synthetic DNA fragment.

Northern Blot Analysis

Poly(A)+ RNA was prepared from the following cell lines: ,βTC1, αTC1 [a transgenically derived glucagon-producing α-cell line (Efrat et al. (1988) *Neuron* 1:605–613)], Ltk- (a mouse fibroblast cell line) and J558L [a mouse myeloma (Oi et al., (1983) *PNAS* 80:825–829)] using the Fast Track kit from Invitrogen Inc. (San Diego, Calif.). Poly(A)+ RNAs from the tissues used were purchased from Clontech Inc. (Palo Alto, Calif.). Electrophoresis of RNA, blotting, stripping, hybridization and random labelling of probes were performed as described previously (Sambrook et al., (1989) *Molecular Cloning: A Laboratory Manual*, supra).

Preparation of Antisera

Anti-IPF1 antiserum was prepared using a DNA fragment encoding the C-terminal half of IPF1 which includes part of the homeodomain. This fragment was inserted into the expression vector path 11 and expressed as a TrpE fusion protein (Klempnauer and Sippel, (1987) *EMBO J* 6:2719–2725; Angel et al., (1988) *Nature* 332:166–171). The fusion protein was purified by preparative SDS-PAGE and used to elicit polyclonal antibodies in rabbits (Thor et al., (1991) *Neuron* 7:1–9). To obtain antibodies that specifically recognized the C-terminal part of Ipf1, the C-terminal part of Ipf1 (amino acids 215–284) lacking any homeodomain residues was expressed as a fusion protein with glutathione S-transferase using the GST gene fusion system in *Escherchia coli* (Smith and Johnson, (1988) *Gene* 67:31–40;

Pharmacia, Uppsala, Sweden). The fusion protein was affinity purified on a glutathione-Sepharose 4B column (Pharmacia, Uppsala, Sweden) and the eluted fusion protein was immobilized on Affi-gel10 (Thor et al., supra). The anti-Ipf1 antiserum was applied to a column containing the immobilized Ipf1 C-terminal fusion protein; after extensive washing, the bound antibodies were eluted, reapplied to an identical column and subsequently eluted (Thor et al., supra).

Immunohistochemistry

Immunohistochemistry on adult mouse pancreas was done on freshly frozen mouse C57BL/6JBom (Bomholtgard Breeding and Research Centre Ltd, Ry, Denmark) pancreas that had been sectioned on a cryostat. Cryosections (8 $\mu$m) were mounted on glass slides, air dried and stored at −80° C. Prior to immunostaining, the sections were fixed in 1% paraformaldehyde (pH 7.4) for 20 min, washed in TBS (50 mM Tris-HCl pH 7.4, 150 mM NaCl) and blocked with 5% normal goat serum in TBST (TBS containing 0.1% Triton X-100) for 10 min. Sectioning of embryos was done by harvesting embryos from timed (Kaufman, 1992), pregnant C57BL/6JBom mice that were either fixed in 1% paraformaldehyde (pH 7.4) for 1–2 h and then frozen (for e8.5–11.5 embryos) or frozen directly (for e12.5–16.5 embryos). The immunohistochemistry on both pancreas and embryos was then carried out as previously described (Thor et al., supra).

Whole-mount Immunohistochemistry

Whole-mount immunohistochemistry was carried out on e8.5–9.5 mouse embryos as described previously (Ruiz I Altaba and Jessel, (1991) *Development* 112:945–958) but with the following modifications. Embryos were fixed in 1% paraformaldehyde, 0.1 M potassium phosphate pH 7.4 for 1–2 h, transferred to 30% sucrose, 0.1 M potassium phosphate, 0.02% sodium azide and stored at +4C. Before staining, the embryos were transferred to TBS for 1 h. The embryos were then blocked for endogenous peroxidase activity in methanol containing 3% hydrogen peroxide for at least 2 h. The blocking solution was then gradually replaced by TBS. Non-specific binding was reduced by incubation in 5% normal goat serum in TBST. Antibodies were diluted in TBST with 5% normal goat serum. The primary antibodies were detected with the ABC immunoperoxidase system according to the manufacturer's recommendation (Vector Laboratories Inc., USA) with the exception that the ABC complex was diluted 5-fold before incubation. After each antibody incubation, embryos were extensively washed in TBST for at least 2 h with four to six changes.

Example 2

Ipf1 Transgenic Mice

In mouse embryos, Ipf1 expression is restricted to the developing pancreatic anlagen and is initiated when the foregut endoderm commits to a pancreatic fate. It is now demonstrated that mice homozygous for a targeted mutation in the Ipf1 gene selectively lack a pancreas. The mutant pups survive fetal development but die within a few days after birth. The gastrointestinal part and all other internal organs were normal in appearance. No pancreatic tissue and no ectopic expression of insulin or pancreatic amylase could be detected in mutant embryos and neonates. These findings show that Ipf1 is needed for the formation of the pancreas and suggest that Ipf1 acts to determine the fate of common pancreatic precursor cells and/or to regulate their propagation.

The mammalian pancreas is a mixed exocrine and endocrine gland that, in most species, arises from ventral and dorsal buds which subsequently merge to form the definitive pancreas. In both mouse and rat, the first histological sign of morphogenesis of the dorsal pancreas is a dorsal evagination of the duodenum at the level of the liver at around 22–25 somite stage, and shortly thereafter a ventral evagination appears as a derivative of the liver diverticulum2–4. Low levels of insulin gene transcripts are already present and restricted to the dorsal foregut endoderm at 20 somites suggesting that pancreas or insulin- gene-specific transcriptional factors are present in this region prior to the onset of morphogenesis.5

Figure 2:
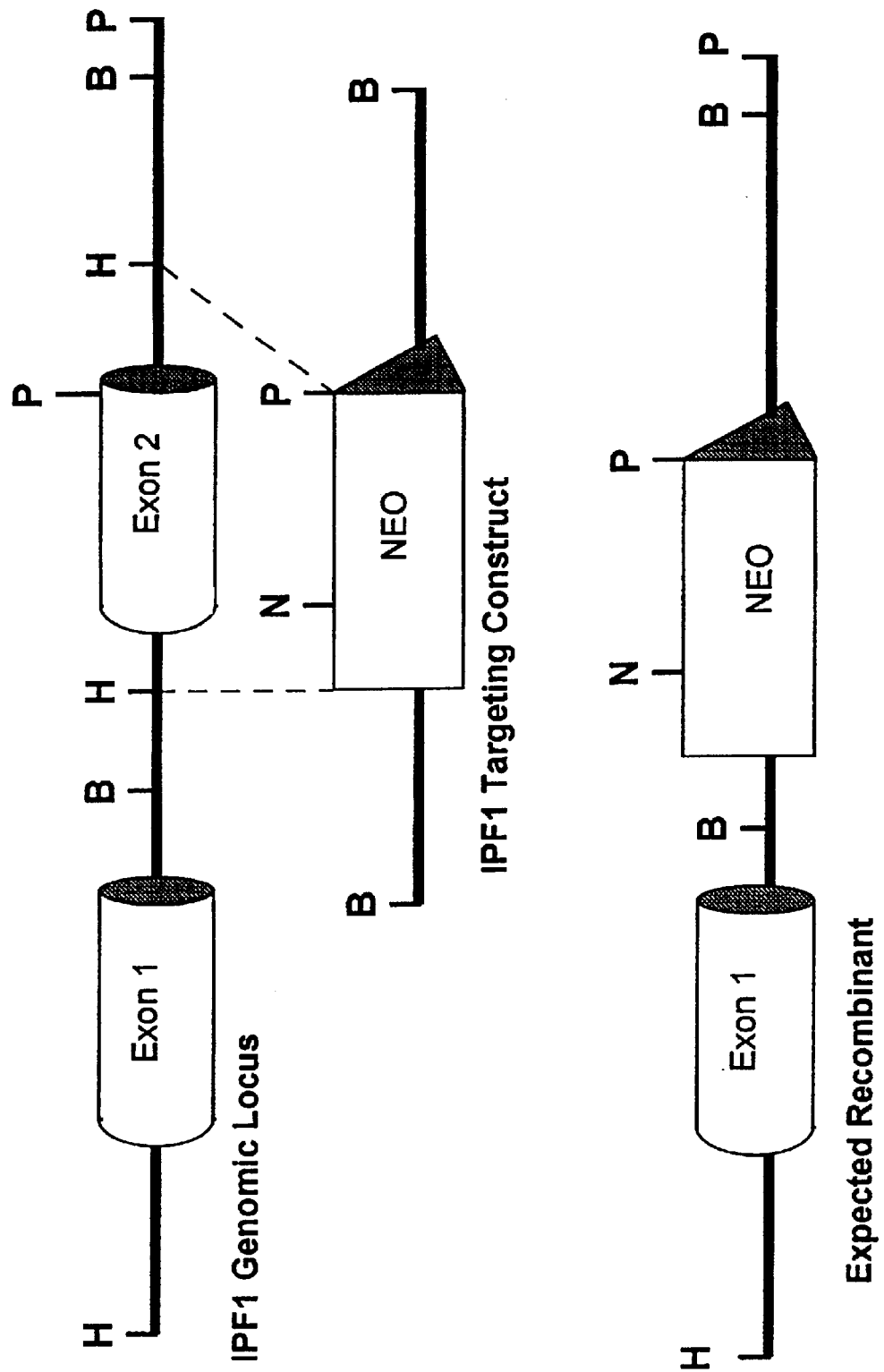
FIG. 2 is a schematic representation of targeting construct, genomic DNA and the expected product of homologous recombination. The two exons of Ipf1 are indicated by cylinders and the bacterial neomycin gene, under control of the herpes simplex virus (HSV) promoter/enhancer, is represented by a triangular bar. Deletion of the 3.1-kb HindIII/NcoI fragment from within the 7.2-kb BamH1 segment of the Ipf1 genomic DNA results in loss of the entire homeobox, the splice acceptor site and parts of the intron. This fragment was replaced with the 1,142-bp Xno1/BamH1 fragment from pMC1 neopoly(A) (Thomas et al. (1987) *Cell* 51:503–512). Restriction enzymes: B, BamH1; H, HindIII; N. NcoI; P. PstI. The mouse Ipf1 gene was cloned from a mouse 129/SV genomic library. E14-1 ES cells were cultured on mitomycin-treated embryonic fibroblasts in medium supplemented with 1,000 U/ml leukaemia-inhibitory factor as previously described (Kuhn et al. (1991) *Science* 254:707–710). A Bio-Rad GenePulser at 500 F, 260 mV was used to electroporate $10^7$ cells with 25 μgml linearized targeting DNA. Cells were plated on mitomycin-treated neomycin-resistant STO fibroblasts. Selection with 250 μgml G418 was initiated after 48 h and ES colonies were picked eight days later. Blastocysts from C57BL/6 mice were injected and transferred to pseudopregnant (C57BL/6×CBA)$F_1$ females to generate chimaeric offspring as described in Hogan et al. in *Manipulating the Mouse Embryo*, (Cold Spring Harbor Laboratory Press, Cold Spring Harbor, N.Y., 1986).

In early mouse embryos, the Ipf1 protein is detected only in the developing pancreas but alter in development and in adult mouse pancreas Ipf1 is selectively expressed in the β-cells where it binds to and transactivates the insulin gene. The structurally related Xenopus XlHbox86 and rat STF-1/IDX-17,8 proteins, are also selectively expressed in the endoderm of the duodenum and the pancreas but at present it is not known if these proteins represent functional homologs of Ipf1. To test the hypothesis that Ipf1 plays a role in the pancreatic commitment of the foregut endoderm, Ipf1-deficient mice were generated by deleting exon 2, which encodes the homeodomain of Ipf1 using homologous recombination in ES-cells (FIG. 2). Mice heterozygous for the Ipf1 mutation show no apparent abnormalities, they are fertile and their offspring show the expected Mendelian frequencies of mutant genotypes indicating that the Ipf1-deficiency does not cause embryonic lethality. However, all homozygous mutant mice die within a few days after birth, showing a complete penetrance of this neonatal mortality phenotype. The targeted Ipf1−/−mutant embryos show no detectable Ipf1 immunoreactivity as analyzed by whole-mount immunohistochemistry using anti-Ipf1 antibodies.

Newborn homozygous mutant mice do not show any morphological abnormalities, except that they appear slightly smaller than wildtype and heterozygous littermates, on average ~80% for newborn pups (n=15), and ~60% for two day old pups (n=15). Most Ipf1-deficient pups are initially able to feed as indicated by the presence of milk in their stomachs, but all die within a few days after birth. To determine if pancreas development was affected in the Ipf1 mutants, histological analyses were performed on new born pups from a cross between heterozygous Ipf1 mutants. The homozygous Ipf1 mutants completely lack a pancreas but the duodenum from which the pancreas normally develops showed the normal C-shaped form. The intestines of the Ipf1−/−pups (n=8) have the same relative length (cm/g body weight) +/− 10%, as the wildtype pups and show no apparent abnormalities except that the loops of the small intestine are positioned somewhat differently in the abdomen compared to the wildtype. In the homozygote mutants (n=8) both the liver, which develops from the same part of the primitive foregut as the pancreas, and the spleen, which is thought to be derived from "pancreatic" mesoderm, also appear normal and show the same relative weight (mg/g body weight) +/− 10%, as the wildtype. The common bile duct and the ventral pancreatic duct are both derived from the hepatic diverticulum of the foregut and the main duct of the pancreas normally fuses with the common bile duct in the duodenal wall and both empty into the duodenal lumen at the major duodenal papilla. In the homozygous mutants there is no pancreatic duct, but the common bile duct is present, indicating that, apart from the lack of a pancreas, the duodenal tract is normally developed. Thus, it may be concluded that Ipf1-deficiency leads to the selective loss of the pancreas. The Ipf1−/−pups that are able to feed and live for more than 2 days show elevated urine glucose levels, ≧55 mM for three day old Ipf1−/−pups (n=7), suggesting that the cause of death is partly due to insulin deficiency. The lack of the other islet hormones and the exocrine digestive enzymes may also contribute to the pathology.

The complete lack of a pancreas indicates that Ipf1 is required early in the development of the pancreas and suggests that Ipf1 acts either at the level of determination or the early differentiation of the pancreas. In normal mice, pancreatic amylase and insulin are highly and specifically expressed in the exocrine and endocrine pancreas, respectively, and the expression of the gut-hormone gastrin can be used to determine the state of differentiation of the intestinal epithelium. To exclude the possibility that in the Ipf1-deficient mice morphogenesis was arrested but cytodifferentiation still occurred, immunohistochemical analysis of mutant and wild-type mouse embryos and neonates was performed. In the mouse, both insulin and amylase expressing cells have accumulated in sufficiently high numbers in the pancreas at around embryonic day e15 to allow reproducible detection by immunohistochemistry. The intestinal epithelium differentiates late in development so expression of gastrin was monitored, in sections of the duodenum, in newborn animals. No pancreatic tissue was present in mutant e15 embryos and neonates and no ectopic expression of insulin and amylase was detected in serial sagital sections of the duodenum of mutant embryos and neonates. Cells expressing gastrin were present in the duodenum from both wildtype and mutant newborn animals. This, and the normal histology of the intestinal epithelium in the mutants indicate that this part of the duodenum develops normally. The lack of pancreatic tissue and of ectopic expression of insulin and pancreatic amylase in the developing duodenum show that both cytodifferentiation and morphogenesis of the pancreas is arrested in the homozygous mutants.

The observed phenotype further suggests that Ipf1 has an early function in the initial stages of pancreas development. A few Ipf1 positive cells can first be detected in the gut region at around the 10–12 somite stages which is when the foregut endoderm commits to a pancreatic fate. This and the lack of a pancreas in the Ipf1-deficient mutants strongly suggest that Ipf1 functions in the determination and/or maintenance of the pancreatic identity of common precursor cells, or in the regulation of their propagation.

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

I claim:

1. A substantially pure preparation of an Insulin promoter factor 1 (Ipf1) polypeptide having a sequence at least 80% identical to an amino acid sequence represented in SEQ ID NO: 2.

2. A method for assaying the phenotype of a cell, comprising detecting in the cell a level of mRNA encoding an Insulin promoter factor 1 (Ipf1) polypeptide, comprises i. providing a probe/primer comprising an oligonucleotide containing a nucleotide sequence which hybridizes under conditions of 0.2×SSC at 50° C. to a sense or antisense sequence of SEQ ID NO: 1 or 5' or 3' flanking sequences naturally associated with said gene;

ii. exposing the probe/primer to nucleic acid of the cell; and iii. detecting, by hybridization of the probe/primer to the nucleic acid, the level of mRNA encoding the Ipf1 polypeptide.

3. A method for assaying the phenotype of a cell, comprising detecting in the cell a level of Insulin promoter factor 1 (Ipf1) polypeptide, wherein the level of Ipf1 polypeptide is detected in an immunoassay and wherein said level of Ipf1 polypeptide is indicative of a phenotype of a cell.

4. The method of claim 2, wherein the Ipf1 polypeptide has an amino acid sequence at least 80% identical to the amino acid sequence of SEQ ID NO: 2.

5. The method of claim 2, wherein the Ipf1 polypeptide has an amino acid sequence at least 90% identical to the amino acid sequence of SEQ ID NO: 2.

6. The method of claim 2, wherein the Ipf1 polypeptide modulates at least one of proliferation, differentiation or survival of a cell which expresses a gene that is transcriptionally regulated by an Ipf1-responsive element (Ipf1-RE).

7. The method of claim 3, wherein the Ipf1 polypeptide has an amino acid sequence at least 80% identical to the amino acid sequence of SEQ ID NO: 2.

8. The method of claim 3, wherein the Ipf1 polypeptide has an amino acid sequence at least 90% identical to the amino acid sequence of SEQ ID NO: 2.

9. The method of claim 3, wherein the Ipf1 polypeptide modulates at least one of proliferation, differentiation or survival of a cell which expresses a gene that is transcriptionally regulated by an Ipf1-responsive element (Ipf1-RE).

10. The Ipf1 polypeptide of claim 1, comprising an amino acid sequence at least 90% identical to an amino acid sequence represented in SEQ ID NO: 2.

11. The Ipf1 polypeptide of claim 1, comprising an amino acid sequence at least 95% identical to an amino acid sequence represented in SEQ ID NO: 2.

* * * * *